(12) United States Patent
Czerniak et al.

(10) Patent No.: US 11,795,512 B2
(45) Date of Patent: Oct. 24, 2023

(54) MULTI-COLOR FISH TEST FOR BLADDER CANCER DETECTION

(71) Applicant: Board of Regents, The University of Texas System, Austin, TX (US)

(72) Inventors: Bogdan Czerniak, Houston, TX (US); Keith Baggerly, Houston, TX (US); Jolanta Bondaruk, Houston, TX (US); Tadeusz Majewski, Houston, TX (US); Colin Dinney, Houston, TX (US); Shizhen Zhang, Houston, TX (US); Yan Wang, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/965,409

(22) PCT Filed: Jan. 30, 2019

(86) PCT No.: PCT/US2019/015830
§ 371 (c)(1),
(2) Date: Jul. 28, 2020

(87) PCT Pub. No.: WO2019/152504
PCT Pub. Date: Aug. 8, 2019

(65) Prior Publication Data
US 2021/0230703 A1 Jul. 29, 2021

Related U.S. Application Data

(60) Provisional application No. 62/623,869, filed on Jan. 30, 2018.

(51) Int. Cl.
*C12Q 1/6886* (2018.01)
*C12Q 1/6841* (2018.01)

(52) U.S. Cl.
CPC ......... *C12Q 1/6886* (2013.01); *C12Q 1/6841* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 9,045,802 B2 | 6/2015 | Halling et al. | |
| 9,290,814 B2 | 3/2016 | Giafis et al. | |
| 2007/0178503 A1* | 8/2007 | Jiang | C12Q 1/6837 435/6.16 |
| 2009/0299640 A1* | 12/2009 | Ellis | C12Q 1/6886 702/19 |
| 2010/0311601 A1* | 12/2010 | Symmans | C12Q 1/6886 506/8 |
| 2014/0294873 A1* | 10/2014 | Ghosh | G01N 33/6872 424/184.1 |
| 2015/0368721 A1 | 12/2015 | Symmans et al. | |
| 2016/0041153 A1* | 2/2016 | Brown | G01N 33/5308 436/501 |
| 2017/0114413 A1* | 4/2017 | Hahn | A61K 45/06 |

OTHER PUBLICATIONS

Cobb et al (Crit Care Med 2002 vol. 30 p. 2711) (Year: 2002).*
"UroVysion bladder cancer kit, product description," Abbott Molecular, located at https://www.abbottmolecular.com/us/products/urovysion.html, downloaded Jul. 11, 2016.
Chekaluk et al., "Identification of nine genomic regions of amplification in urothelial carcinoma, correlation with stage, and potential prognostic and therapeutic value," *PLoS ONE*, 8(4):e60927, 2013.
Czerniak et al., "Genetic modeling of human urinary bladder carcinogenesis," *Genes Chromosomes Cancer*, 27:392-402, 2000.
Dal Moro et al., "Urinary markers in the everyday diagnosis of bladder cancer," *Urologia*, 80(4):265-275, 2013.
Liu et al., "Coexistence of YWHAZ amplification predicts better prognosis in muscle-invasive bladder cancer with CDKN2A or TP53 loss," Oncotarget, 7(23):34752-34758, 2016.
Lopez et al., "Identification of prefoldin amplification (1q23.3-q24.1) in bladder cancer using comparative genomic hybridization (CGH) arrays of urinary DNA," *Journal of Translational Medicine*, 11:182, 2013.
Mazzucchelli et al., "Chromosomal abnormalities in macroscopically normal urothelium in patients with bladder pT1 and pT2a urothelial carcinoma: a fluorescence in situ hybridization study and correlation with histologic features," *Anal Quant Cytol Histol.*, 27:143-151, 2005.
Nikonova et al., "Aurora A kinase (AURKA) in normal and pathological cell division," *Cell Mol Life Sci.*, 70:661-687, 2013.
Park et al., "Quantitation of Aurora kinase A gene copy number in urine sediments and bladder cancer detection," *J Natl Cancer Inst.*, 100:1401-1411, 2008.
Patmore et al., "Can a genetic signature for metastatic head and neck squamous cell carcinoma be characterized by comparative genomic hybridization?" *British Journal of Cancer*, 90:1976-1982, 2004.
PCT International Preliminary Report on Patentability issued in International Application No. PCT/US2019/015830, dated Aug. 13, 2020.
PCT International Search Report and Written Opinion issued in International Application No. PCT/US2019/015830, dated Apr. 30, 2019.
Phillips et al., "Aneuploidy in bladder cancers: the utility of fluorescent in situ hybridization in clinical practice," *BJU Int.*, 98:33-37, 2006.
Robertson et al., "Comprehensive Molecular Characterization of Muscle-Invasive Bladder Cancer," *Cell*, 171(3):540-556, 2017.
Shen et al., "6p22.3 amplification as a biomarker and potential therapeutic target of advanced stage bladder cancer," *Oncotarget*, 4(11):2124-2134, 2013.
Sokolova et al., "The development of a multitarget, multicolor fluorescence in situ hybridization assay for the detection of urothelial carcinoma in urine," *J Mol Diagn.*, 2:116-123, 2000.
Zaharieva et al., "High-throughput tissue microarray analysis of 11q13 gene amplification (CCND1, FGF3, FGF4, EMS1) in urinary bladder cancer," *Journal of Pathology*, 201:603-608, 2003.

* cited by examiner

*Primary Examiner* — Katherine D Salmon
(74) *Attorney, Agent, or Firm* — Parker Highlander PLLC

(57) ABSTRACT

The present disclosure provides methods and compositions for the detection of bladder in a subject using four locus-specific probes to 6p22, 8q22, 11q13, and 20p11.2.

12 Claims, 36 Drawing Sheets

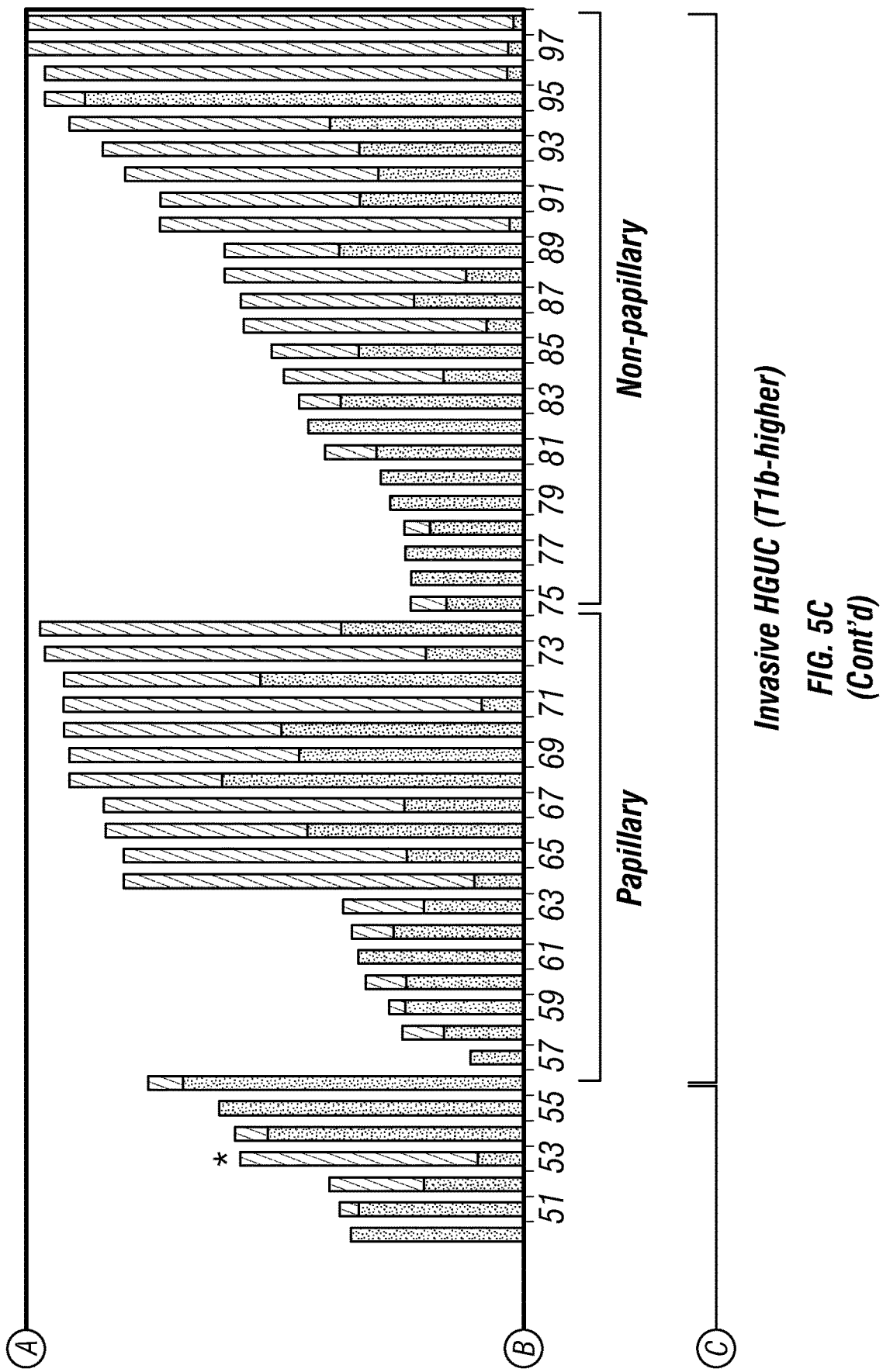

*Superficial LGPUC (Ta-T1a)*

MULTI-COLOR FISH TEST FOR BLADDER CANCER DETECTION

The present application is a national phase application under 35 U.S.C. § 371 of International Application No. PCT/US2019/015830, filed Jan. 30, 2019, which claims the priority benefit of U.S. Provisional Application Ser. No. 62/623,869, filed Jan. 30, 2018, the entire contents of each of which are hereby incorporated by reference.

This invention was made with government support under grant numbers CA091846 and CA151489 awarded by the National Institutes of Health. The government has certain rights in the invention.

BACKGROUND

1. Field

The present invention relates generally to the fields of molecular biology and medicine. More particularly, it concerns chromosomal regions with copy number variation in bladder cancer.

2. Description of Related Art

Malignant cells frequently acquire chromosomal instability, manifested as increased or decreased copy numbers of entire chromosomes and their segments, referred to as aneuploidy (Sansregret and Swanton, 2017). Aneuploidy has been proposed to drive tumor development by altering cellular phenotypes responsible for such fundamental aspects of malignant transformation as increased cellular proliferation, invasion, and metastasis (Naylor and van Deursen, 2016). Aneuploidy emerges early in the process of cancer development and can be detected in in situ preneoplastic conditions such as dysplasia and carcinoma in situ or even in adjacent microscopically normal tissue referred to as field effects (Mazzucchelli et al., 2005). Ergo, aneuploidy represents an attractive target for explorations of novel early diagnostic and preventive strategies (Phillips et al., 2006).

Bladder cancer is among the most common human malignancies that show pronounced features of genomic instability, exhibiting a heavy mutational load and widespread copy number variations affecting numerous chromosomes, which makes it an obvious target for diagnostic explorations (Robertson et al., 2017). Previous studies have shown that anomalies in genes linked to organelles responsible for segregation of chromosomes and their regulatory mechanisms, such as Aurora Kinase A (AURKA), contribute to the genomic instability and aggressive behavior of bladder cancer (Nikonova et al., 2013). AURKA copy numbers have also been used as effective biomarkers for bladder cancer detection in voided urine. AURKA copy numbers and other multicolor fluorescent in situ hybridization (FISH) tests assessing chromosomal copy numbers (based predominantly on assays of centromeric probes) in exfoliated cells of voided urine samples have been used in clinical practice as non-invasive detection tests for bladder cancer, as has urine cytology (Park et al., 2008). They have also been applied to monitor the recurrence and progression of patients with non-muscle invasive bladder tumors. The sensitivity and specificity of the existing tests are not, however, sufficiently high to eliminate or even reduce the frequency of the need for invasive cystoscopy and tissue biopsy to rule out clinically evident bladder cancer (Dal Moro et al., 2013). The most popular FISH-based test was designed nearly two decades ago and was based on pregenomic data (Sokolova et al., 2000). It utilizes predominantly centromeric probes and a probe for 9p deletions. Recent genomic analyses provide comprehensive molecular characterization of bladder cancer and permit the identification of multiple specific chromosomal loci amplified in bladder cancer, which may be used as biomarker targets. Tests developed with such biomarkers may offer enhanced diagnostic performance and may be subjected to improvements by selecting multiple alternative combination of the diagnostic probes.

Defining the molecular mechanisms that underlie bladder cancer invasion and metastasis could identify biomarkers predicting the presence of metastases and therapeutic targets that could be used to block the progression of the disease, dramatically altering the outcome. Gene copy number could be used as an effective biomarker for the non-invasive detection of bladder cancer, such as by fluorescence in situ hybridization (FISH). Thus, there is an unmet need for improved methods for the non-invasive detection and monitoring of bladder cancer using gene copy number.

SUMMARY

In a first embodiment, there is provided an in vitro method of detecting the presence of four probes comprising obtaining a set of locus-specific probes for 6p22, 8q22, 11q13, and 20p11.2; hybridizing the set of locus-specific probes to a plurality of nucleic acids; and analyzing the hybridization pattern of the set of locus-specific probes to the plurality of nucleic acids, thereby detecting the presence of the four probes.

In some aspects, the plurality of nucleic acids are obtained from a biological sample. In certain aspects, the biological sample is a surgical specimen, biopsy specimen, a paraffin embedded tissue, a frozen tissue imprint, peripheral blood, a bladder washing, barbotage, renal pelvic brushes, conduit urine, voided urine, or a fine needle aspirate. In specific aspects, the biological sample is voided urine.

In some aspects, the biological sample is obtained from a subject at risk for cancer. In certain aspects, the subject has not been previously diagnosed with cancer. In particular aspects, the cancer is bladder cancer.

In certain aspects, hybridizing is further defined as performing fluorescence in situ hybridization (FISH). In some aspects, the probes are labeled with a detectable label. In specific aspects, the detectable label is a fluorophore. In some aspects, each probe is labeled with a distinct fluorophore. In particular aspects, the distinct fluorophores are green, gold, red, and blue. In some aspects, the distinct fluorophores have excitation at 495 nm, 530 nm, 590 nm, and 415 nm.

In some aspects, analyzing comprises quantifying the copy number of each of the locus-specific probes. In certain aspects, an abnormal copy number of one or more (e.g., 2, 3, or 4) of the locus-specific probes indicates the presence of cancer. In certain aspects, an abnormal copy number of all four of the locus-specific probes indicates the presence of cancer. In some aspects, an abnormal copy number of all four the locus-specific probes indicates cancer recurrence, cancer progression, or an unfavorable response to therapy. In certain aspects, an abnormal copy number of all four the locus-specific probes indicates a high grade tumor. In some aspects, the abnormal copy number is further defined as three or more copies of one or more probes. In some aspects, the abnormal copy number is further defined as three or more copies of each of the four probes.

In some aspects, at least 15% (e.g., 20%, 30%, 40%, 45%, or 50%) of cells in the sample comprise the abnormal copy number. In particular aspects, at least 50% (e.g., 60%, 70%, 80%, or more) of cells in the sample comprise the abnormal copy number.

In particular aspects, the sensitivity of detecting cancer is at least 75%, such as at least 76%, 77%, 78%, 79%, 80%, or higher. In some aspects, the specificity of detecting cancer is at least 90%, such as 91%, 92%, 93%, 94%, 95%, 96%, 97%, 98%, 99%, or 100%.

In another embodiment, there is provided a method of treating cancer in a subject comprising administering one or more anti-cancer therapies to the subject, wherein the subject is identified to have an abnormal copy number at the loci 6p22, 8q22, 11q13, and 20p11.2.

In some aspects, the abnormal copy number at the four loci is determined by performing FISH on a sample obtained from the subject. In particular aspects, the abnormal copy number at the four loci is determined according to the methods of the embodiments (e.g., obtaining a set of locus-specific probes for 6p22, 8q22, 11q13, and 20p11.2; hybridizing the set of locus-specific probes to a plurality of nucleic acids; and analyzing the hybridization pattern of the set of locus-specific probes to the plurality of nucleic acids, thereby detecting the presence of the four probes). In certain aspects, the sample is a voided urine sample. In particular aspects, the cancer is bladder cancer. In some aspects, the one or more anti-cancer therapies are chemotherapy, radiotherapy, gene therapy, surgery, hormonal therapy, anti-angiogenic therapy, and/or immunotherapy. In some aspects, the anti-cancer therapy is a molecularly targeted therapy.

Also provided herein is a composition comprising an effective amount of an anti-cancer therapy for the treatment of bladder cancer in a subject, wherein the subject is identified to have an abnormal copy number at the loci 6p22, 8q22, 11q13, and 20p11.2. In some aspects, the anti-cancer therapy is chemotherapy, radiotherapy, gene therapy, surgery, hormonal therapy, anti-angiogenic therapy, and/or immunotherapy. In some aspects, the anti-cancer therapy is a molecularly targeted therapy.

A further embodiment provides a kit for detecting cancer comprising a set of locus-specific probes to 6p22, 8q22, 11q13, and 20p11.2. In some aspects, each locus-specific probe is labeled with a distinct fluorophore. In certain aspects, the distinct fluorophores have excitation at 495 nm, 530 nm, 590 nm, and 415 nm.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

The patent or application file contains at least one drawing executed in color. Copies of this patent or patent application publication with color drawings(s) will be provided by the Office upon request and payment of the necessary fee.

(FIG. 2A) Circos diagram summarizing CNV analysis of bladder cancer tumor samples from the MDACC cohort (n=40). (FIG. 2B) Top 10 most frequently amplified chromosomal regions validated in the TCGA cohort (n=126). (FIG. 2C) Top 10 most significantly amplified chromosomal regions validated in the TCGA cohort. (FIG. 2D) Frequency histograms of amplifications of four chromosomes selected to design the FISH probes for the Quartet Test.

(FIG. 3A) Dual color FISH with centromeric and respective chromosomal probes 6p22 E2F3, 8q22 YWHAZ, 11q13 FGF3, and 20q11 MAPRE13. (FIG. 3B) Hybridization signals for a mixture of four probes (6p22 E2F3, green Platinum Bright™495, 8q22 YWHAZ, gold Platinum Bright™530, 11q13 FGF3, dark red, Platinum Bright™590, and 20q11 MAPRE13, blue, Platinum Bright™415) showing the hybridization signals on their respective human metaphase chromosomes. (FIG. 3C) Hybridization signals obtained with a mixture of the four probes listed above (the Quartet Test) in normal human urothelial cells. (FIG. 3D) Hybridization signals obtained with a mixture of four probes comprising the Quartet Test in a cell from a touch print prepared from a tumor tissue of a high grade bladder cancer. Multiple copies of each probe were detected.

(FIG. 4A) Representative FISH images of low-grade papillary urothelial carcinoma. Upper row shows representative images of tissue samples. Lower row shows representative images of paired voided urine samples of the same patient. Multiple copies of each probe were detected. (FIG. 4B) Quantitative assessment of the percentage of cells with abnormal copy number in paired samples of low-grade papillary urothelial carcinoma and voided urine of the same patient. (FIG. 4C) Representative FISH images of high-grade urothelial carcinoma. Upper row shows representative images of tissue samples. Lower row shows representative images of paired voided urine samples of the same patient. (FIG. 4D) Quantitative assessment of the percentage of cells with abnormal copy number in paired samples of high grade urothelial carcinoma and voided urine of the same patient.

(FIG. 5A) Percentage of cells with abnormal copy number in individual samples of 48 benign controls dichotomized into groups with low levels of amplification (3-4 copies for at least one probe) and high levels of amplification (more than four copies for at least one probe). (FIG. 5B) Percentage of cells with abnormal copy number in individual samples of 48 controls separated into four groups according to the numbers of probes with abnormal copy numbers. (FIG. 5C) Percentage of cells with abnormal copy number in individual samples of 98 voided urines from patients with bladder cancer dichotomized into groups with low levels of amplification (3-4 copies for at least one probe) and high levels of amplification (more than four copies for at least one probe). *Indicate T1a tumors. (FIG. 5D) Percentage of cells with abnormal copy number separated into four groups according to the numbers of probes with abnormal copy numbers in individual samples of 98 voided urines from patients with bladder cancer separated into four groups according to the number of probes with abnormal copy numbers. *Indicate T1a tumors.

(FIG. 6A) Receiver operating characteristic curve (ROC) based on the proportion of cells with abnormal copy number for the set consisting of 98 urine samples from patients with bladder cancer and 48 urine samples from control subjects (18 healthy controls and 30 with benign non-neoplastic disorders of the urinary tract). The Quartet Test for the detection of bladder cancer showed an area under the receiver operating characteristic curve (AUC) of 0.902 (95% confidence interval [CI]=0.854-0.949). Sample 13 showed cells with 3-4 and more than 4 probes. (FIG. 6B) Box plot analysis of mean percentage of abnormal cells in benign control samples and two groups of bladder cancer dichotomized into a superficial low-grade papillary carcinoma (LGPUC, $T_a$-$T_{1a}$) and high-grade invasive carcinoma (HGUC, $T_{1b}$-higher). Sample 12 showed 4 probes, sample 17 showed both 1 and 2 probes, and sample 33 showed 3 probes. (FIG. 6C) Average proportion of cells in voided urine showing 3-4 or more than four copies for at least one probe in benign controls, LGPUC ($T_a$-$T_{1a}$) and HGUC ($T_{1b}$-higher) groups of samples. (FIG. 6D) Average proportion of cells with increased copy numbers of 1-4 probes in benign controls, LGPUC ($T_a$-$T_{1a}$) and HGUC ($T_{1b}$-higher) groups of samples. (FIG. 6E) Box plot analysis of the QS values in benign controls, LGPUC ($T_a$-$T_{1a}$) and HGUC ($T_{1b}$-higher) groups of samples. (FIG. 6F) Receiver operating characteristic curve (ROC) based on the QS values for the set consisting of 98 urine samples from patients with bladder cancer and 48 urine samples from control subjects (18 healthy controls and 30 with benign non-neoplastic disorders of the urinary tract). The QS values of the Quartet Test for the detection of bladder cancer showed an area under the AUC 0.908 and CI=0.861-0.954).

(FIG. 8A) Top 10 most frequently amplified chromosomal regions. (FIG. 8B) Top 10 most significantly amplified chromosomal regions.

(FIG. 11A) ROC based on the proportion of cells with abnormal copy number for the set consisting of voided urine samples from 56 patients with low-grade and 42 patients with high-grade bladder cancers. The Quartet Test using the proportion of abnormal cells for the assessment of bladder cancer grade showed AUC of 0.897 (95% CI 0.835-0.959). (FIG. 11B) ROC based on QS for the set consisting of voided urine samples from 56 patients with lowgrade and 42 patients with high-grade bladder cancers. The Quartet Tests using QS for the assessment of bladder cancer grade showed AUC of 0.890 (95% CI 0.816-0.963). (FIG. 11C) Logistic regression analysis (LRA) of the Quartet Test results using the proportion of abnormal cells and QS to assess the grade of the tumor. Proportion of abnormal cells correlated with high grade tumor.

(FIG. 12B) Mean and standard error of the mean values for the proportion of abnormal cells in 19 cases of voided urine samples from patients with bladder cancer based on the assessment of four independent observers. (FIG. 12C) Quantitative score in 19 cases of voided urine samples from patients with bladder cancer assessed by four independent observers. (FIG. 12D) Mean and standard error for the quantitative score in 19 cases of voided urine samples from patients with bladder cancer assessed by four independent observers. (FIG. 12E) Box plot of the proportion of abnormal cells in 19 cases of voided urine samples from patients with bladder cancer assessed by four independent observers. (FIG. 12F) Box plot of the quantitative score in 19 cases of voided urine samples from patients with bladder cancer assessed by four independent observers.

DESCRIPTION OF ILLUSTRATIVE EMBODIMENTS

Figure 1:
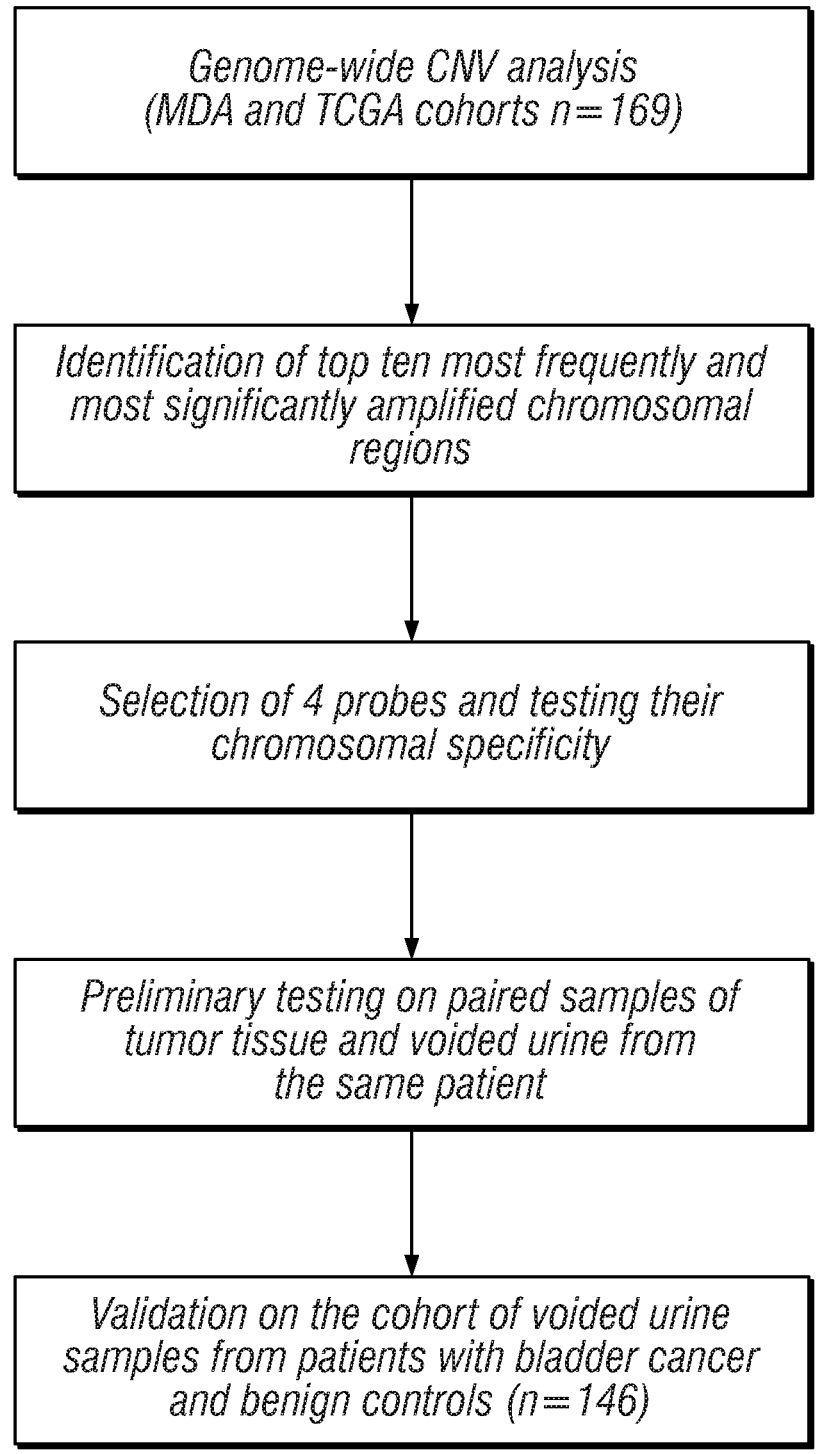
FIG. 1: Overall plan for the development and testing of the Quartet Test.

The present studies used genomics analysis and unique whole-organ mapping data for the identification and validation of chromosomal regions of copy number variation in bladder cancer patients. Samples were initially analyzed by using a fraction of abnormal cell scores and then by quantitative score which included not only the proportion of cells with abnormal copy number but also the proportion of cells with the number of altered copies and degree of amplification. Receiver operator characteristic curves were used to identify cut-off values for the scores at which the performances of sensitivity and specificity were maximized.

The studies led to the development of a novel multicolor FISH test, referred to as the Quartet Test, which includes four specific chromosomal probes aimed at the loci 6p22, 8q22, 11q13, and 20q11.2. These loci were identified by genome-wide analysis of copy number variations and were frequently amplified in bladder cancer. The copy number status assessed by probes detected in voided urine reflected the amplification status of the primary tumor. An ROC curve summarizing the proportion of assayed cells with any abnormal copy numbers gave specificity of 93.8% and a sensitivity of 78.6% by using the proportion of cells with abnormal copy numbers. Quantitative score giving extra weight to cells with multiple simultaneous amplifications provided 95.8% specificity and 76.8% sensitivity. Both percentage of abnormal cells and quantitative scores were highly effective for assessing the grade of the tumor.

Assay validation was performed on urine samples from 98 patients with bladder cancer: 56 with low-grade papillary, 42 with high-grade invasive disease, and 48 benign controls. Therefore, the present assay can improve the detection of bladder cancer as well as the management of patients with already diagnosed disease by decreasing the number of invasive cytoscopic surveillance procedures required.

Thus, in certain embodiments, the present disclosure provides a sensitive method for the detection of cancer, particularly bladder cancer, comprising FISH analysis of four locus-specific probes to chromosomal regions 6p22, 8q22, 11q13, and 20p11.2. Specifically, the Quartet Test can be used for noninvasive detection of bladder cancer in voided urine. In one method, the locus-specific probes are hybridized to cells (e.g., a urine sample) on a slide. In general, in situ hybridization includes the steps of fixing a biological sample, hybridizing a chromosomal probe to target DNA contained within the fixed biological sample, washing to remove non-specific binding, and detecting the hybridized probe. Microscopic analysis is then performed to determine the presence of cells with an abnormal copy number (i.e., three or more copies of any given locus) of the chromosomal regions. If the loci for all four probes are found to have abnormal copy numbers, then the sample is determined to indicate the presence of bladder cancer. In further methods, the set of locus-specific probes provided herein may be used for determining the risk of cancer recurrence, assessing the grade of the tumor, predicting cancer progression or response to therapy (i.e., post-treatment effects).

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. The terms "about", "substantially" and "approximately" mean, in general, the stated value plus or minus 5%.

As used herein, the term "subject" refers to a human or non-human mammal or animal. Non-human mammals include livestock animals, companion animals, laboratory animals, and non-human primates. Non-human subjects also specifically include, without limitation, chickens, horses, cows, pigs, goats, dogs, cats, guinea pigs, hamsters, mink, and rabbits. In some embodiments of the invention, a subject is a patient. As used herein, a "patient" refers to a subject who is under the care of a physician or other health care worker, including someone who has consulted with, received advice from or received a prescription or other recommendation from a physician or other health care worker.

The term "treatment" or "treating" is intended to include prophylaxis, amelioration, prevention or cure of a condition (e.g., bladder cancer). Treatment after a condition (e.g., bladder cancer) that has started aims to reduce, ameliorate or altogether eliminate the condition, and/or its associated symptoms, or prevent it from becoming worse. Treatment of subjects before a condition has started aims to reduce the risk of developing the condition and/or lessen its severity if the condition does develop. As used herein, the term "prevent" refers to the prophylactic treatment of a subject who is at risk of developing a condition resulting in a decrease in the probability that the subject will develop the disorder, and to the inhibition of further development of an already established disorder.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

A "probe" or "probes" refers to a polynucleotide that is at least eight (8) nucleotides in length and which forms a hybrid structure with a target sequence, due to complementarity of at least one sequence in the probe with a sequence in the target region. The polynucleotide can be composed of DNA and/or RNA. Probes in certain embodiments, are detectably labeled. Probes can vary significantly in size. Generally, probes are, for example, at least 8 to 15 nucleotides in length. Other probes are, for example, at least 20, 30 or 40 nucleotides long. Still other probes are somewhat longer, being at least, for example, 50, 60, 70, 80, or 90 nucleotides long. Probes can be of any specific length that falls within the foregoing ranges as well. Preferably, the probe does not contain a sequence complementary to the sequence(s) used to prime for a target sequence during the polymerase chain reaction.

"Oligonucleotide" or "polynucleotide" refers to a polymer of a single-stranded or double-stranded deoxyribonucleotide or ribonucleotide, which may be unmodified RNA or DNA or modified RNA or DNA.

II. BLADDER CANCER DETECTION

A. Biological Sample

Certain embodiments of the present disclosure concern the hybridization of locus-specific probes to cells in a sample. As used herein, the term "biological sample" may refer to a whole organism or a subset of its tissues, cells or component parts. A "biological sample" may also refer to a homogenate, lysate, or extract prepared from a whole organism or a subset of its tissues, cells or component parts, or a fraction or portion thereof. Typically, the biological sample is concentrated prior to hybridization to increase cell density. Non-limiting examples of biological samples include urine, blood, cerebrospinal fluid (CSF), pleural fluid, sputum, and peritoneal fluid, bladder washings, secretions (e.g., breast secretion), oral washings, tissue samples, touch preps, or fine-needle aspirates. In some embodiments, a biological sample may be a cell line, cell culture or cell suspension. Preferably, a biological sample corresponds to the amount and type of DNA and/or expression products present in a parent cell from which the sample was derived. A biological sample can be from a human or non-human subject. Chromosomal preparations are prepared from biological samples according to standard protocols. In some embodiments, the sample used for performing FISH is a formalin fixed paraffin embedded (FFPE) specimen, touch preparation, or voided urine sample.

The sample may comprise body fluids and tissue samples that include but are not limited to blood, tissue biopsies, spinal fluid, meningeal fluid, urine, alveolar fluid. In particular embodiments, the sample is a voided urine sample. For those tissue samples in which the cells do not naturally exist in a monolayer, the cells can be dissociated by standard techniques known to those skilled in the art. These techniques include but are not limited to trypsin, collagenase or dispase treatment of the tissue.

Typically, cells are harvested from a biological sample using standard techniques. For example, cells can be harvested by centrifuging a biological sample such as urine, and resuspending the pelleted cells. Typically, the cells are resuspended in phosphate-buffered saline (PBS). After centrifuging the cell suspension to obtain a cell pellet, the cells can be fixed, for example, in acid alcohol solutions, acid acetone solutions, or aldehydes such as formaldehyde, paraformaldehyde, and glutaraldehyde. For example, a fixative containing methanol and glacial acetic acid in a 3:1 ratio, respectively, can be used as a fixative. A neutral buffered formalin solution also can be used, and includes approximately 1% to 10% of 37-40% formaldehyde in an aqueous solution of sodium phosphate. Slides containing the cells can be prepared by removing a majority of the fixative, leaving the concentrated cells suspended in only a portion of the solution.

The cell suspension is applied to slides such that the cells do not overlap on the slide. Cell density can be measured by a light or phase contrast microscope. For example, cells harvested from a 20 to 100 ml urine sample typically are resuspended in a final volume of about 100 to 200 µl of fixative. Three volumes of this suspension (usually 3, 10, and 30 µl), are then dropped into 6 mm wells of a slide. The cellularity (i.e. density of cells) in these wells is then assessed with a phase contrast microscope. If the well containing the greatest volume of cell suspension does not have enough cells, the cell suspension is concentrated and placed in another well.

Prior to in situ hybridization, chromosomal probes and chromosomal DNA contained within the cell each are denatured. Denaturation typically is performed by incubating in the presence of high pH, heat (e.g., temperatures from about 70° C. to about 95° C.), organic solvents such as formamide and tetraalkylammonium halides, or combinations thereof. For example, chromosomal DNA can be denatured by a combination of temperatures above 70° C. (e.g., about 73° C.) and a denaturation buffer containing 70% formamide and 2×SSC (0.3M sodium chloride and 0.03 M sodium citrate). Denaturation conditions typically are established such that cell morphology is preserved. Chromosomal probes can be denatured by heat. For example, probes can be heated to about 73° C. for about five minutes.

After removal of denaturing chemicals or conditions, probes are annealed to the chromosomal DNA under hybridizing conditions. "Hybridizing conditions" are conditions that facilitate annealing between a probe and target chromosomal DNA. Hybridization conditions vary, depending on the concentrations, base compositions, complexities, and lengths of the probes, as well as salt concentrations, temperatures, and length of incubation. The higher the concentration of probe, the higher the probability of forming a hybrid. For example, in situ hybridizations are typically performed in hybridization buffer containing 1-2×SSC, 50% formamide and blocking DNA to suppress non-specific hybridization. In general, hybridization conditions, as described above, include temperatures of about 25° C. to about 55° C., and incubation lengths of about 0.5 hours to about 96 hours.

Non-specific binding of chromosomal probes to DNA outside of the target region can be removed by a series of washes. Temperature and concentration of salt in each wash depend on the desired stringency. For example, for high stringency conditions, washes can be carried out at about 65° C. to about 80° C., using 0.2× to about 2×SSC, and about 0.1% to about 1% of a non-ionic detergent such as Nonidet P-40 (NP40). Stringency can be lowered by decreasing the temperature of the washes or by increasing the concentration of salt in the washes.

B. Chromosomal Probes

Certain embodiments of the present disclosure concern locus-specific probes that hybridize to a chromosomal regions 6p22 (e.g., E2F3, CDKAL1), 8q22 (e.g., YWHAZ, PABPC1, ZNF706), 11q13 (e.g., FGF3, FGF4, FGF19), and 20p11.2 (e.g., MAPRE1). The four chromosomal probes provide greater sensitivity and specificity than use of any one locus-specific probe. Based on the detection of abnormal copy number (i.e., more than two copies of each probe) for the four locus-specific probes, a subject can be identified to have a cancer, particularly bladder cancer.

In some aspects, the probes comprise distinct fluorophore wavelengths, particularly wavelengths which do not overlap. In one example, the 6p22 probe (i.e., E2F3—CDKAL1, 525 KB) may be green, such as Platinum Bright™495, the 8q22 probe (i.e., PABPC1-ZNF706, 480 KB) may be gold, such as Platinum Bright™530, the 11q13 probe (i.e., FGF19-FGF3) may be dark red, such as Platinum Bright™590, and the 20q11.2 probe (i.e., MAPRE1, 610 KB) may be blue, such as Platinum Bright™415.

Chromosomal probes are typically about 50 to about $1 \times 10^5$ nucleotides in length. Longer probes typically comprise smaller fragments of about 100 to about 500 nucleotides in length. Probes that hybridize with locus-specific DNA are available commercially, for example, from Vysis, Inc. (Downers Grove, Ill.), Molecular Probes, Inc. (Eugene, Oreg.), or from Cytocell (Oxfordshire, UK). Alternatively, probes can be made non-commercially from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, U.S. Pat. No. 5,491,224.

The locus-specific probes typically are directly labeled with a fluorophore, an organic molecule that fluoresces after absorbing light of lower wavelength/higher energy. The fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, U.S. Pat. No. 5,491,224.

Fluorophores of different colors are chosen such that each chromosomal probe in the set can be distinctly visualized. For example, a combination of the following fluorophores may be used: 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, and Cascade™ blue acetylazide (Molecular Probes, Inc., Eugene, Oreg.). Probes are viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the chromosomal probes.

Probes also can be indirectly labeled with biotin or digoxygenin, or labeled with radioactive isotopes such as $^{32}P$ and $^3H$, although secondary detection molecules or further processing then is required to visualize the probes. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard calorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

C. In Situ Hybridization

Aspects of the invention relate to the use of fluorescent in situ hybridization to detect the four locus-specific probes to 6p22, 8q22, 11q13, and 20p11.2. FISH is used to detect highly specific DNA probes which have been hybridized to chromosomes using fluorescence microscopy. The DNA probe is labeled with fluorescent or non-fluorescent molecules which are then detected by fluorescent antibodies. The probes bind to a specific region or regions on the target chromosome. The chromosomes are then stained using a contrasting color, and the cells are viewed using a fluorescence microscope. Each FISH probe is specific to one region of a chromosome, and is labeled with fluorescent molecules.

In one exemplary method, FISH is performed by first breaking apart (i.e., denature) the double strands of DNA in both the probe DNA and the chromosome DNA so they can bind to each other. This is done by heating the DNA in a solution of formamide at a high temperature (e.g., 70-75° C.) Next, the probe is placed on the slide and the slide is placed in a 37° C. incubator overnight for the probe to hybridize with the target chromosome. Overnight, the probe DNA seeks out the corresponding target sequence on the specific chromosome and binds to it. The strands then slowly reanneal. The slide is washed in a salt/detergent solution to remove any of the probe that did not bind to chromosomes and differently colored fluorescent dye is added to the slide to stain all of the chromosomes so that they may then be viewed using a fluorescent light microscope. Two, or more different probes labeled with different fluorescent tags can be mixed and used at the same time. The chromosomes are then stained with a third color for contrast. This technique allows, for example, the localization of genes and also the direct morphological detection of genetic defects. In particular aspects, FISH allows for the detection of abnormal copy number of a given locus.

As used herein "fluorescent in situ hybridization" or "FISH" refers to a method for detecting or localizing a specific DNA sequence on a chromosome through the use of a labeled nucleic acid probe that hybridizes to a specific DNA sequence on a chromosome. As used herein a "nucleic acid probe" refers to a nucleic acid (such as DNA, RNA, PNA etc.) sequence that recognizes and hybridizes to a specific DNA sequence on a chromosome.

FISH assays rely on detecting hybridization between a nucleic acid probe and a specific DNA sequence on a chromosome. As used herein "hybridization" refers to the process of joining two complementary strands of DNA or RNA, or hybrids thereof, to form a double-stranded molecule. The hybridization step may involve one, two, or multiple probes. It will be appreciated that hybridization conditions may need to be determined empirically for different probes. Hybridization conditions can be varied, producing a range of high to low stringency conditions, as will be known to those of ordinary skill in the art. Several factors can be manipulated experimentally in order to optimize hybridization, including but not limited to temperature, salt concentration, formamide concentration, and presence of other components such as dextran sulfate (as discussed in US Patent Publication US2005/0100944). These factors and others can be varied during hybridization steps and during subsequent wash steps in order to optimize hybridization signals for a given probe and sample. General conditions for in situ hybridization are discussed in Leitch et al., 1994. Higher stringency conditions generally result in lower background signals for probe detection, but can also decrease sensitivity. In some embodiments high stringency conditions may consist of 0.1×SSPE, 0.1% SDS, 65° C.; medium stringency conditions may consist of 0.2×SSPE, 0.1% SDS, 50° C.; and low stringency conditions may consist of 1×SSPE, 0.1% SDS, 50° C. (as discussed in US Patent Publication US2006/0199213). It will be appreciated that many possible variations of these conditions, and many other components including a variety of buffers and salts will be compatible with the instant invention.

In one aspect, the present disclosure provides a method of screening for cancer in a subject. The method includes the steps of hybridizing a set of locus-specific probes to a biological sample from the subject; selecting cells from the biological sample; determining the presence or absence of abnormal copy number of the four loci in the selected cells; and correlating the presence of abnormal copy number of the four loci in the selected cells with cancer in the subject. The biological sample can be urine, blood, cerebrospinal fluid, pleural fluid, sputum, peritoneal fluid, bladder washings, oral washings, tissue samples, touch preps, or fine-needle aspirates, and can be concentrated prior to use. Urine is a particularly useful biological sample. The cells can be selected by nuclear morphology including nucleus size and shape. Nuclear morphology can be assessed by DAPI staining. The method is useful for detecting cancers such as bladder cancer, lung cancer, breast cancer, ovarian cancer, prostate cancer, colorectal cancer, renal cancer, and leukemia. The present methods are particularly suited for detecting bladder cancer.

In some embodiments, a nucleic acid probe for use in a FISH assay, is generated from a BAC (bacterial artificial chromosome) clone, such as one available from the BAC PAC Resources Center (BPRC) at the Children's Hospital Oakland Research Institute, Oakland, Calif. As used herein a "BAC" refers to a vector used to clone DNA fragments in *Escherichia coli* cells. BACs typically contain 50-300 kb DNA inserts. In other embodiments a nucleic acid probe for use in a FISH assay can be generated from a fosmid. As used herein a "fosmid" refers to a cloning vector based on the bacterial F-plasmid. In certain embodiments a probe is generated from multiple fosmids that are pooled together. It should be appreciated that the length of an optimal probe for a FISH assay may need to be empirically determined. In some embodiments the length of a probe is between 80-150 kbp. It should further be appreciated that other sources of large DNA fragments would also be compatible with probe generation for FISH assays, and accordingly, with methods of the instant invention. Smaller DNA fragments are also compatible with methods of the instant invention, and in some embodiments are pooled together (as described above for fosmids).

According to aspects of the present disclosure, a nucleic acid probe is labeled with a tag or label. In some embodiments the tag or label for use in a FISH assay is a fluorescent tag or label, also referred to as a fluorophore. Any appropriate technique for labeling a nucleic acid, as would be understood by one of ordinary skill in the art, is compatible with the instant disclosure. In some embodiments, the nucleic acid probe is labeled through nick translation, according to standard protocols. In other embodiments, the nucleic acid probe is labeled through random priming, according to standard protocols. In further embodiments, the nucleic acid probe is labeled through end labeling, according to standard protocols. It should be appreciated that any tag or label that can be used to label a nucleic acid probe may be compatible with the instant invention. In some embodiments the tag is selected from, but is not limited to, SpectrumRed-dUTP, SpectrumGreen-dUTP, SpectrumGreen-11-dUTP, and SpectrumOrange-dUTP, all available from Abbott Molecular, Des Plaines, Ill. In some embodiments, a probe may be labeled with biotin or digoxigenin.

A positive hybridization signal in a FISH assay is detected by visualization of the tag accompanying the nucleic acid probe, through fluorescence microscopy. In some embodiments the first nucleic acid probe is tagged with a fluorescent tag such as SpectrumRed-dUTP, while the second nucleic acid probe is tagged with a different fluorescent tag such as SpectrumGreen-dUTP.

In some embodiments, a FISH assay will involve a test sample and a control sample. In some embodiments a control sample may be a wild-type or normal chromosomal preparation, while the test sample may be a sample in which the presence of abnormal copy number for the four loci 6p22, 8q22, 11q13, and 20p11.2.

D. Methods of Use

Aspects of the present disclosure include methods for diagnosing or monitoring the onset, progression, or regression of cancer in a subject by, for example, obtaining cell or tissue samples from a subject and assaying such samples for the presence of abnormal copy number of the four loci 6p22, 8q22, 11q13, and 20p11.2. As used herein, the term "cancer" refers to an uncontrolled growth of cells that may interfere with the normal functioning of the bodily organs and systems, and includes both primary and metastatic tumors. Primary tumors or cancers that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject.

Cancers include, but are not limited to, basal cell carcinoma, biliary tract cancer; bladder cancer; bone cancer; brain and CNS cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas. In particular embodiments, a subject who is diagnosed or treated by the present methods, is a subject with bladder cancer.

In some embodiments, the results of the FISH analysis to detect the presence or absence of abnormal copy number of the four loci 6p22, 8q22, 11q13, and 20p11.2, will be used in diagnosis of bladder cancer. In other embodiments, the results of the FISH analysis to identify the presence or absence of abnormal copy number of the four loci 6p22, 8q22, 11q13, and 20p11.2 will be used in classification of the subject as exhibiting a poor, intermediate or good bladder cancer prognosis based on the results of the FISH analysis or used in classification of low grade or high grade bladder cancer.

The methods described herein can be used to screen patients for cancer, or can be used to monitor patients diagnosed with cancer. For example, in a screening mode, patients at risk for bladder cancer, such as patients older than 50 who smoke, or patients chronically exposed to aromatic amines, are screened with the goal of earlier detection of bladder cancer. The methods described herein can be used alone, or in conjunction with other tests, such as the hemoglobin dipstick test. For example, a patient having an increased risk of bladder cancer can be screened for bladder cancer by detecting hemoglobin in the urine, i.e., hematuria. During such a screening process, patients without hematuria do not need further analysis, and are instead, re-examined for hematuria in an appropriate amount of time, e.g., at their annual check-up. Samples from patients with hematuria are further analyzed using the methods described herein. In general, a set of chromosomal probes is hybridized with the biological sample, and the presence of abnormal copy number is determined in the selected cells. Patients that have abnormal copy number at the four loci are further examined, for example, by cystoscopy, and can receive appropriate treatment, if necessary. After treatment, patients are monitored for cancer recurrence using the methods described herein.

In some embodiments, a test sample may be a sample from a subject who has bladder cancer or a precancerous condition, while a control sample may be a sample from a cell or subject that is free of cancer and/or free of a precancerous condition. In these embodiments, detection of an abnormal copy number in the test sample but not in the control sample may indicate that the test sample came from a subject who has bladder cancer or a precancerous condition. In some embodiments, a control sample may be a sample that is from a cell or subject that is known to have bladder or a precancerous condition exhibiting an abnormal copy number. In these embodiments, detection of an abnormal copy number in the test sample and in the control sample may indicate that the test sample came from a subject who has bladder cancer or a precancerous condition. In some embodiments, a control sample may be a bladder cancer cell line that does contain an abnormal copy number of the four loci.

It should be appreciated that performance of a FISH assay to detect abnormal copy number of the four loci 6p22, 8q22, 11q13, and 20p11.2 for diagnosis or prognosis of bladder cancer may be combined with analysis of other markers, or other diagnostic or prognostic assays. In some embodiments, other assays may be conducted in combination with, or following a FISH assay, for further confirmation, or for further analysis of the molecular basis of the abnormal copy number.

E. Anti-Cancer Agents

In some embodiments, the present methods identify a subject to have a cancer, such as bladder cancer, by detecting abnormal copy number of the four loci 6p22, 8q22, 11q13, and 20p11.2. In further embodiments, the present disclosure provides methods of treating a subject identified to have a cancer by administering one or more anti-cancer therapies.

The one or more anti-cancer therapies may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The anti-cancer therapy may be in the form of adjuvant or neoadjuvant therapy.

In some embodiments, the anti-cancer therapy is the administration of small molecule enzymatic inhibitor or anti-metastatic agent. In some embodiments, the anti-cancer therapy is the administration of side-effect limiting agents (e.g., agents intended to lessen the occurrence and/or severity of side effects of treatment, such as anti-nausea agents, etc.). In some embodiments, the anti-cancer therapy is radiation therapy. In some embodiments, the anti-cancer therapy is surgery. In some embodiments, the anti-cancer therapy is a combination of radiation therapy and surgery. In some embodiments, the anti-cancer therapy is gamma irradiation. In some embodiments, the anti-cancer therapy is therapy targeting PBK/AKT/mTOR pathway, HSP90 inhibitor, tubulin inhibitor, apoptosis inhibitor, and/or chemopreventative agent. The anti-cancer therapy may be one or more of the chemotherapeutic agents known in the art.

A first anti-cancer therapy may be administered before, during, after, or in various combinations relative to an additional cancer therapy, such as immune checkpoint therapy. The administrations may be in intervals ranging from concurrently to minutes to days to weeks. In embodiments where the first anti-cancer therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the first anti-cancer therapy and the second anti-cancer therapy within about 12 to 24 or 72 h of each other and, more particularly, within about 6-12 h of each other. In some situations, it may be desirable to extend the time period for treatment significantly where several days (2, 3, 4, 5, 6, or 7) to several weeks (1, 2, 3, 4, 5, 6, 7, or 8) lapse between respective administrations.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation, and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies include immune adjuvants, e.g., *Mycobacterium bovis, Plasmodium falciparum*, dinitrochlorobenzene, and aromatic; cytokine therapy, e.g., interferons α, β, and γ, IL-1, GM-CSF, and TNF; gene therapy, e.g., TNF, IL-1, IL-2, and p53; and monoclonal antibodies, e.g., anti-CD20, anti-ganglioside GM2, and anti-p185. It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAGS), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example, it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Publication Nos. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyteassociated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129; International Patent Publication Nos. WO 01/14424, WO 98/42752, and WO 00/37504 (CP675,206, also known as tremelimumab; formerly ticilimumab); U.S. Pat. No. 6,207,156 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in U.S. Pat. No. 8,017,114; incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. No. 5,844,905; incorporated herein by reference, and immunoadhesins such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used alone or in combination with other anti-cancer therapies to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

III. KIT

Also within the scope of the present disclosure are kits for performing FISH assays on chromosomal preparations to detect a cancer, such as bladder cancer. An example of such a kit may include a set of locus-specific probes for 6p22, 8q22, 11q13, and 20p11.2. The kit may further comprise instructions for use of the probes for performing a fluorescent in situ hybridization (FISH) assay to identify abnormal copy number of the four loci within a chromosomal preparation. The kit may further comprise instructions for diagnostic purposes, indicating that a positive identification of abnormal copy numbers of the four loci in a chromosome preparation from a cancer patient indicates a positive diagnosis of bladder cancer. The kit may further comprise instructions that indicate that a positive identification of an abnormal copy number of the four loci in a chromosome preparation from a cancer patient indicates that a patient should be treated with anti-cancer agent for bladder cancer.

In some embodiments, a kit may further comprise a DNA counterstain such as DAPI. In some embodiments, a kit may further comprise reagents and buffers including but not limited to hybridization buffers and/or wash buffers. In some embodiments, a kit may further comprise mounting media and/or one or more control slides.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Detection of Bladder Cancer in Urine Sediments

Figure 2A:
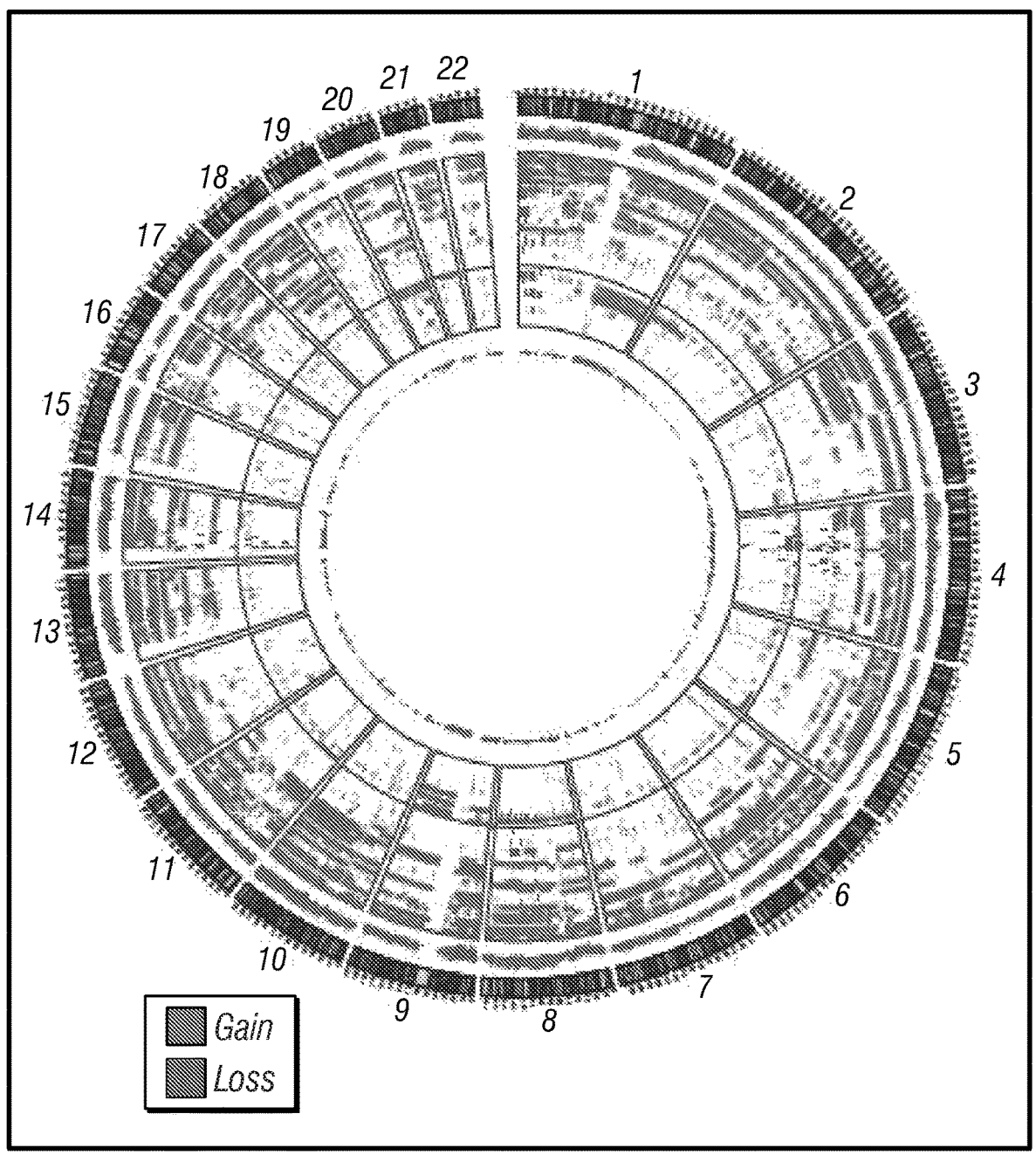
FIGS. 2A-2D: Copy number analysis of bladder cancer cohorts.
Figure 2B:
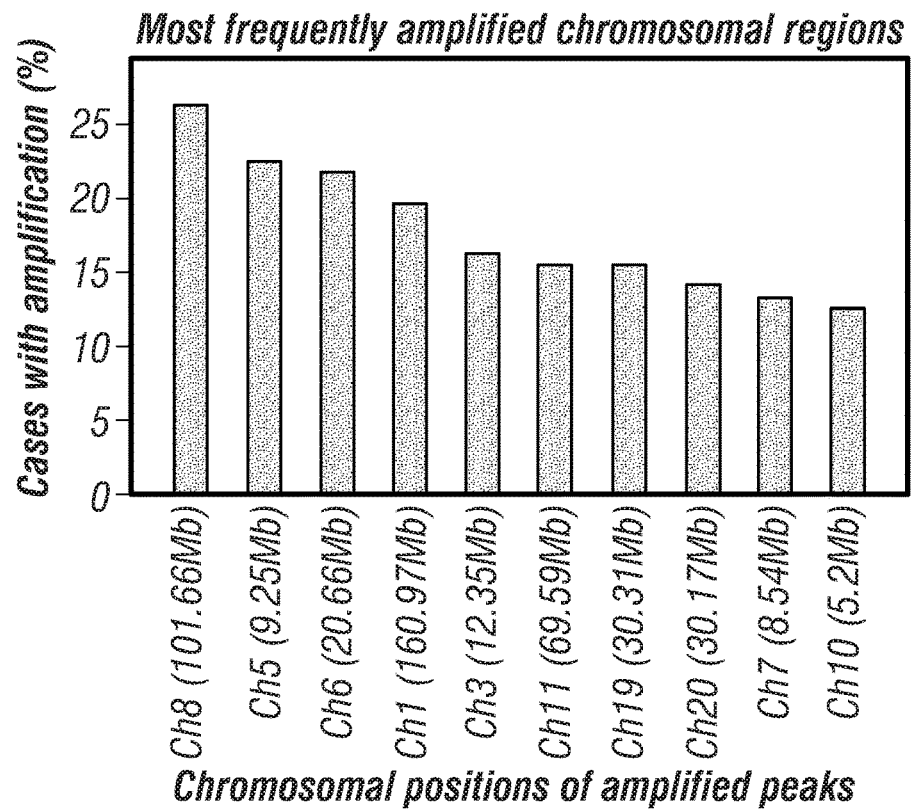
Figure 2C:
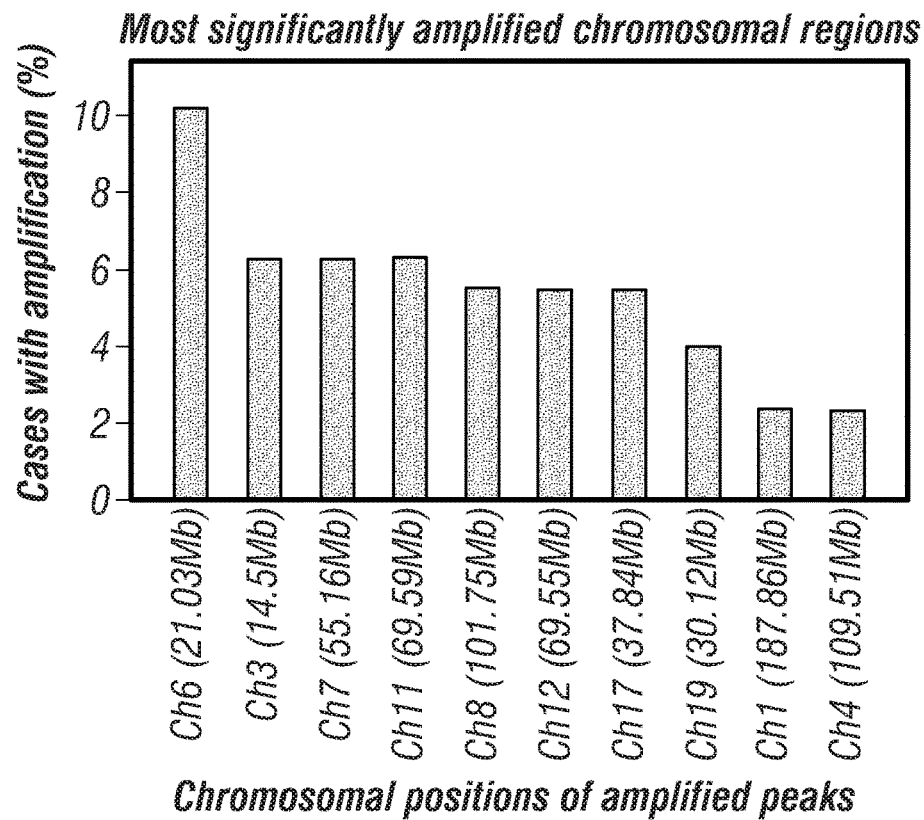
Figure 2D:
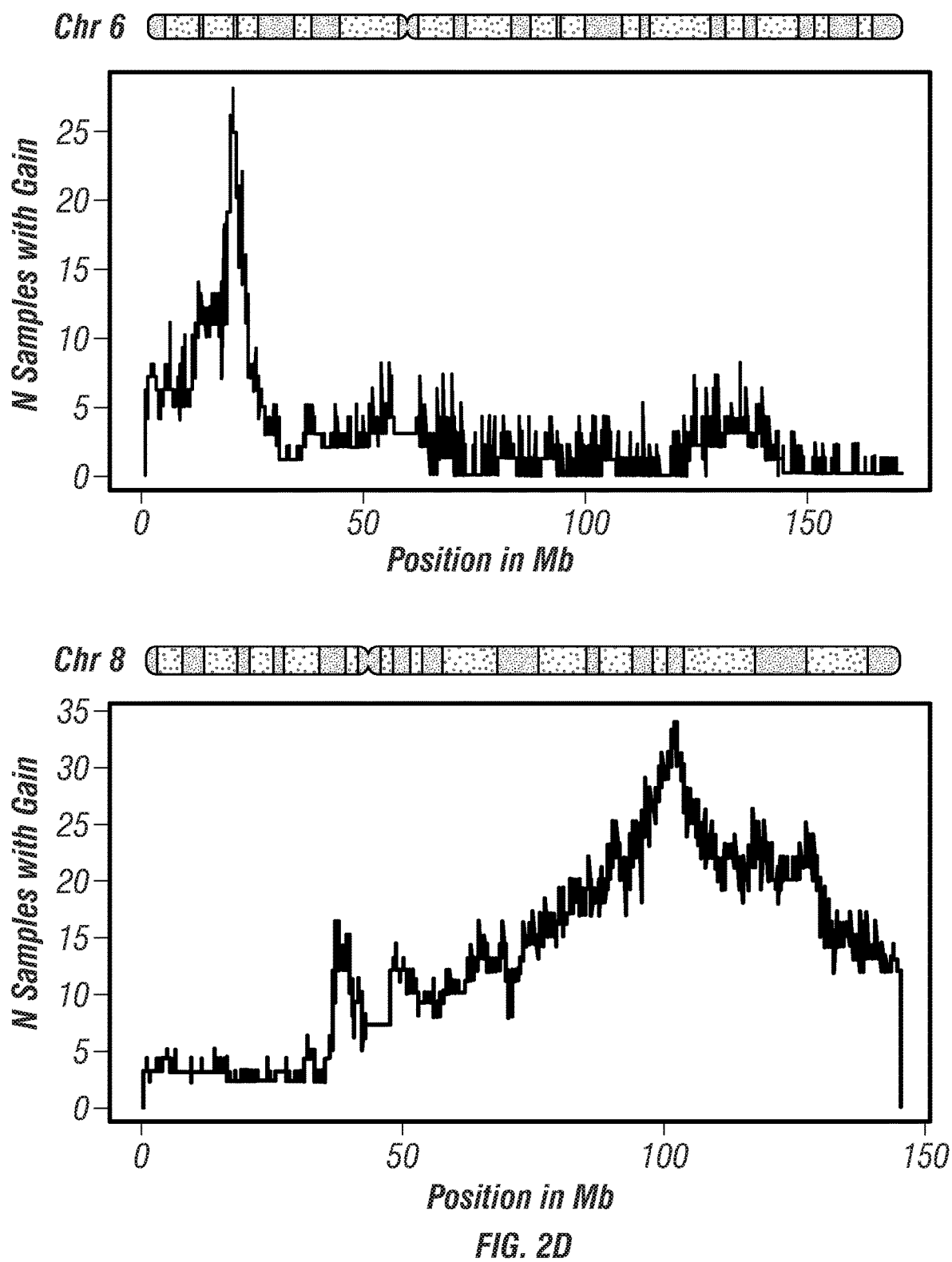
Figure 2D:
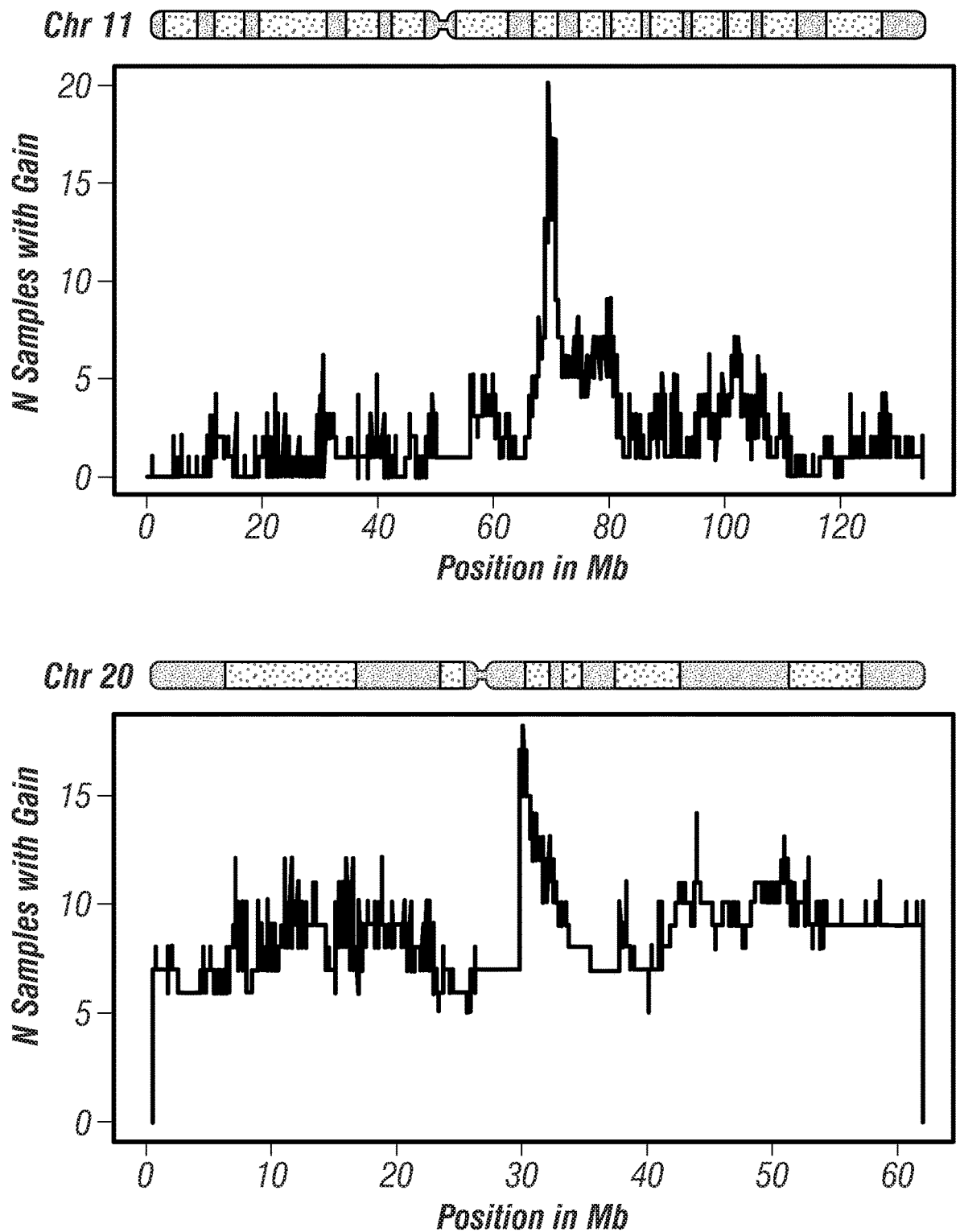
Figure 3B:
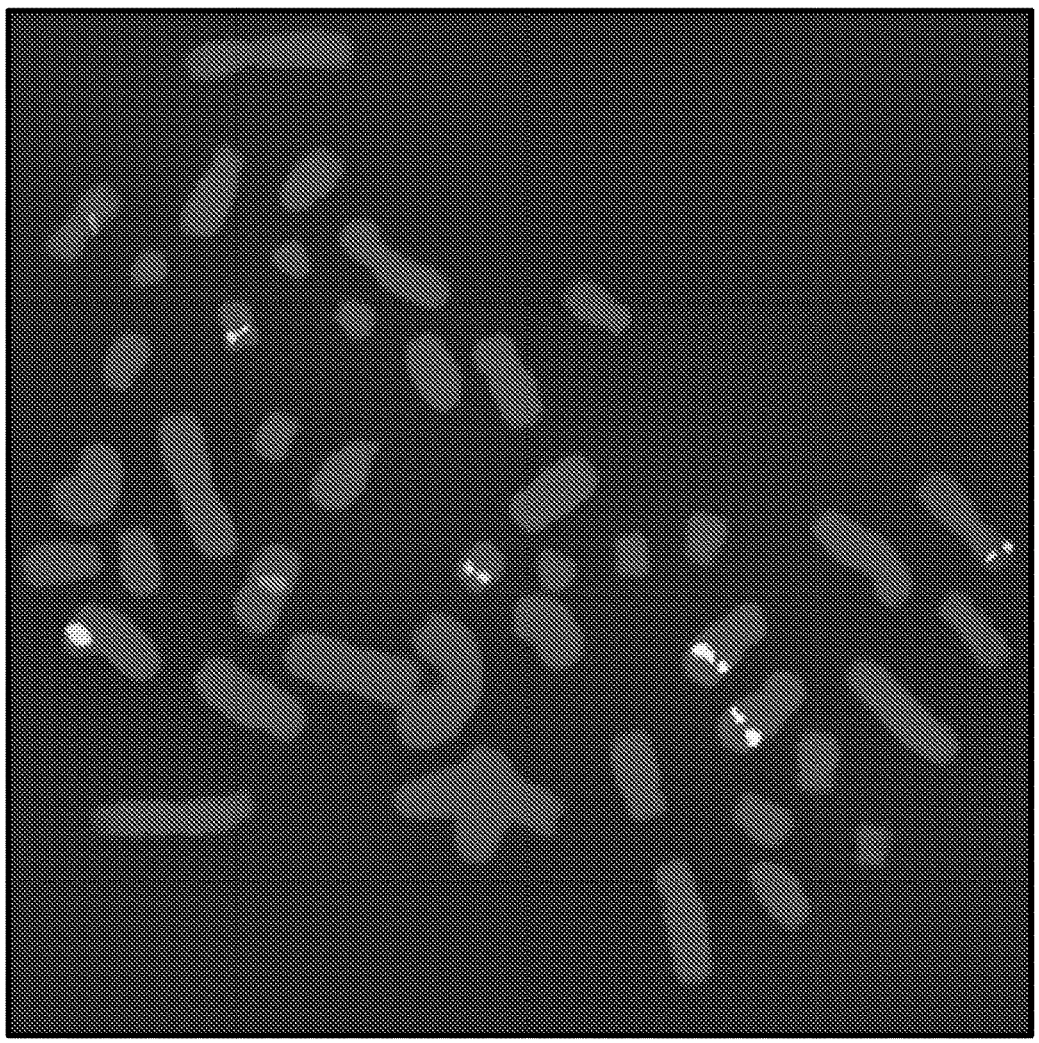
FIGS. 3A-3D: Testing of specificity for chromosomal FISH probes selected to design the Quartet Test.
Figure 3A:
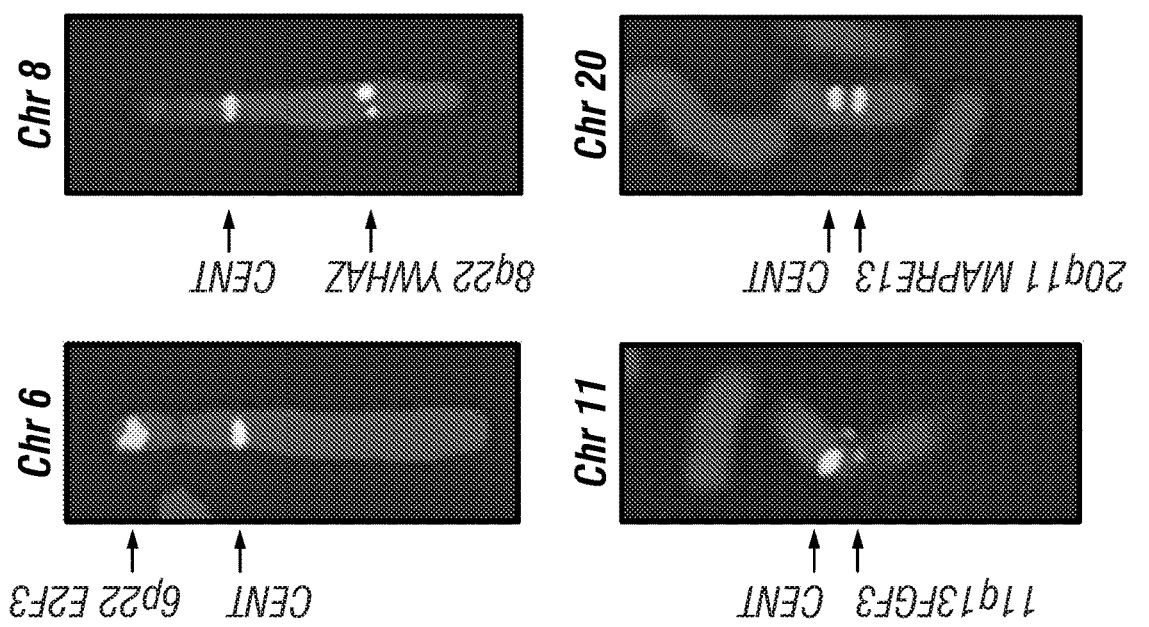
Figure 3D:
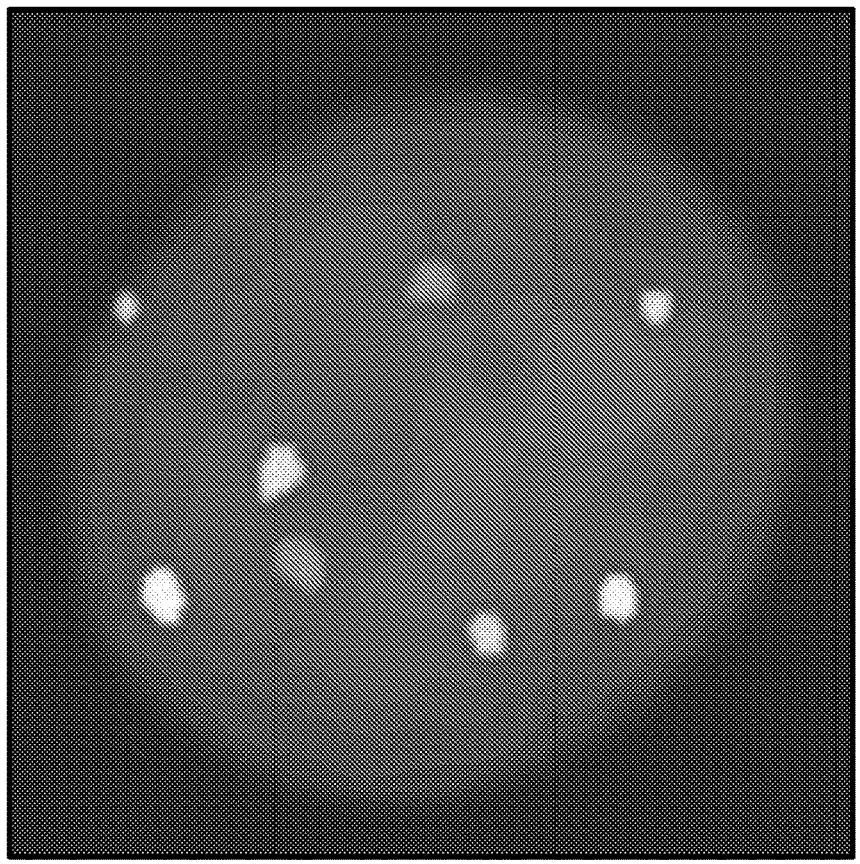
Figure 3C:
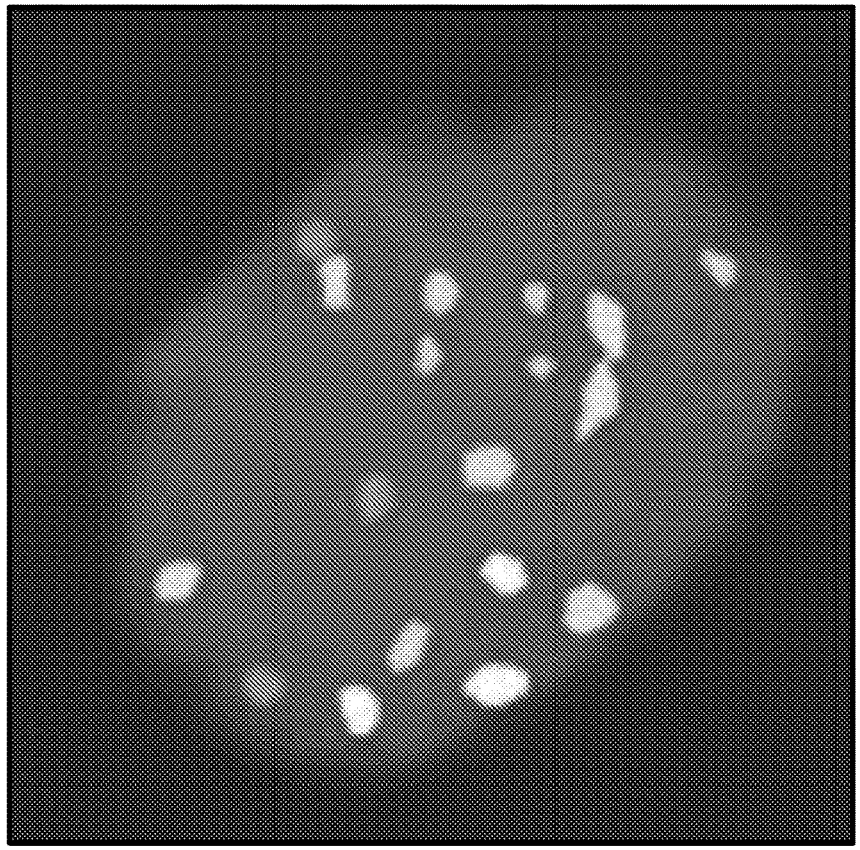
Figure 4A:
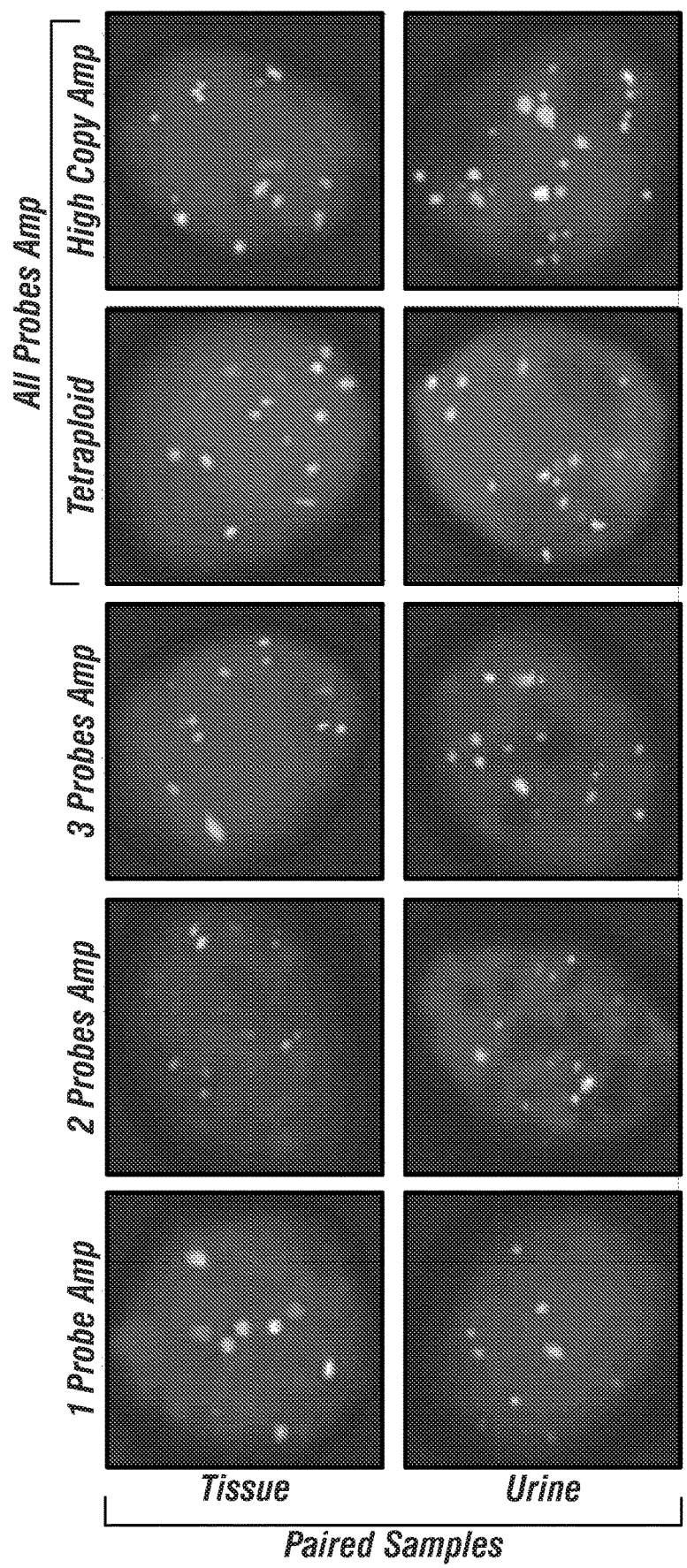
FIGS. 4A-4D: Quantitative assessment of abnormal cells in pairs of tumor tissue and voided urine of the same patients in low- and high-grade urothelial carcinoma by the Quartet Test.
Figure 4B:
Figure 4C:
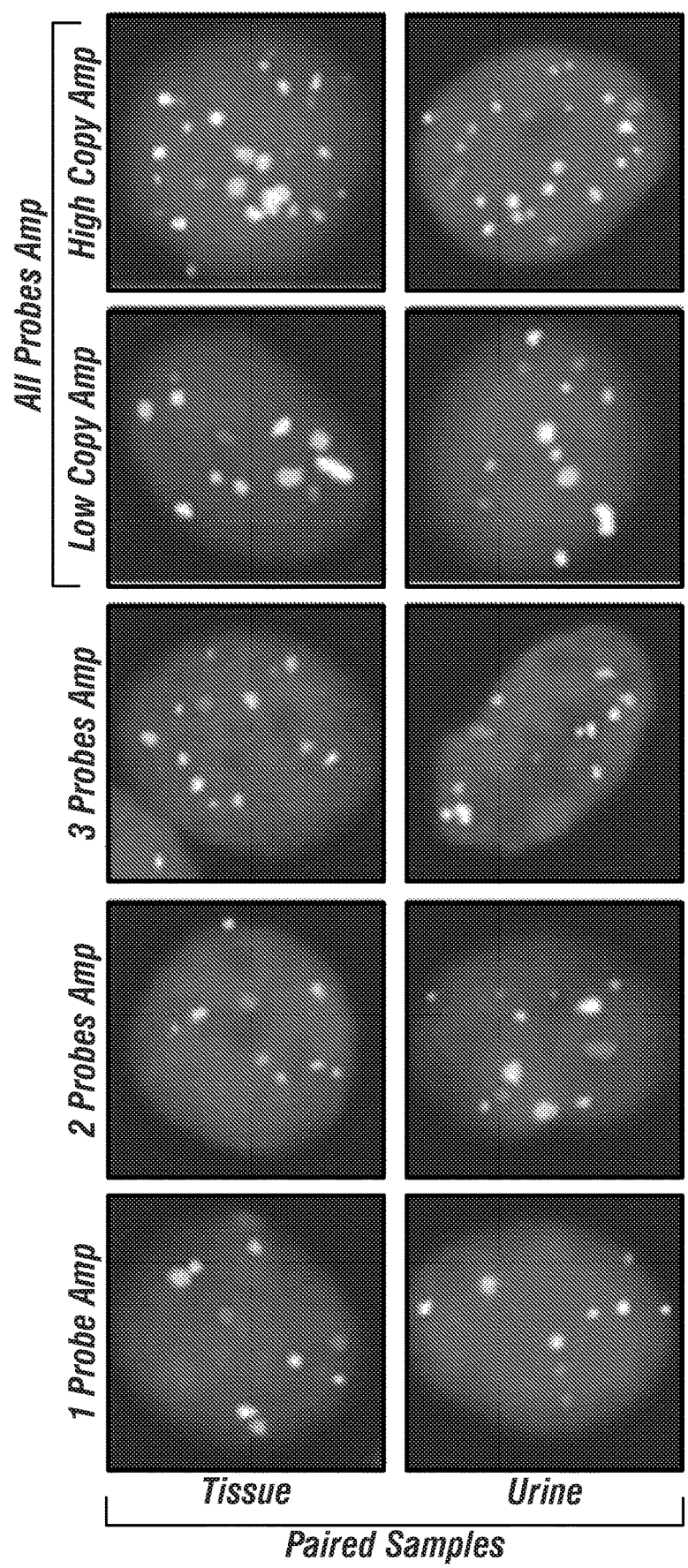
Figure 4D:
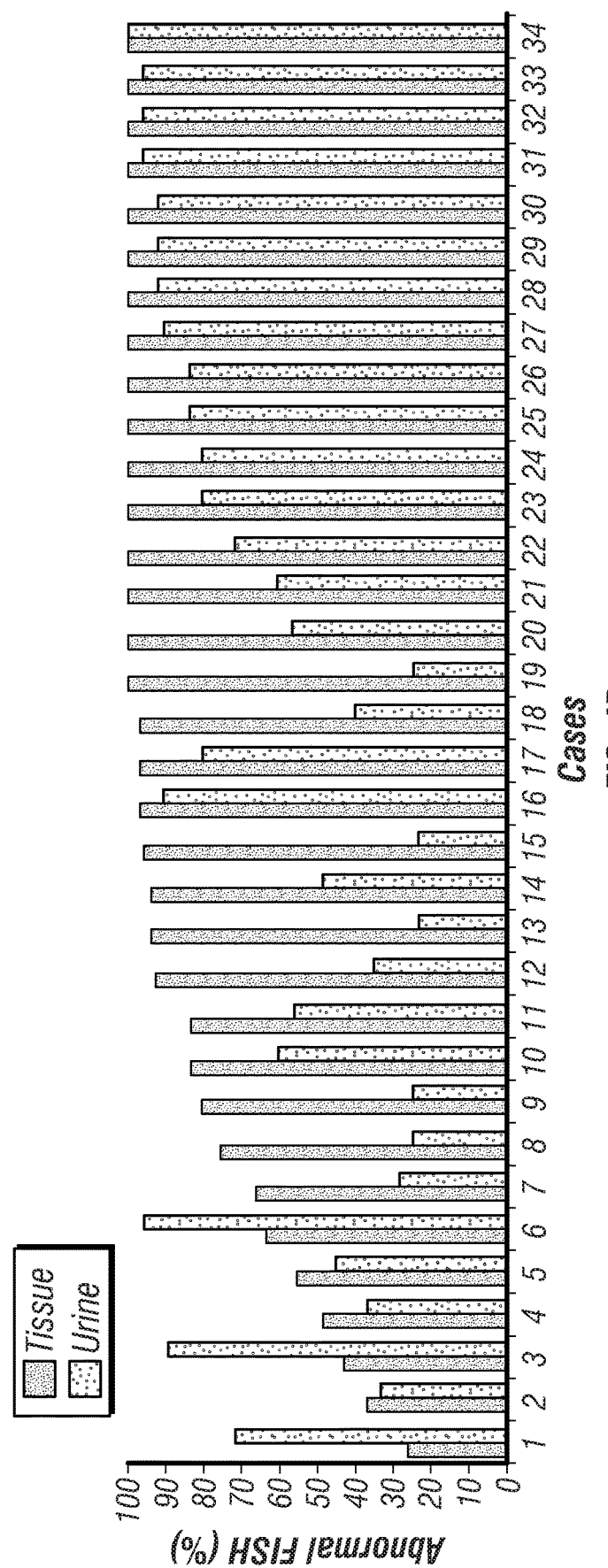
Figure 8A:
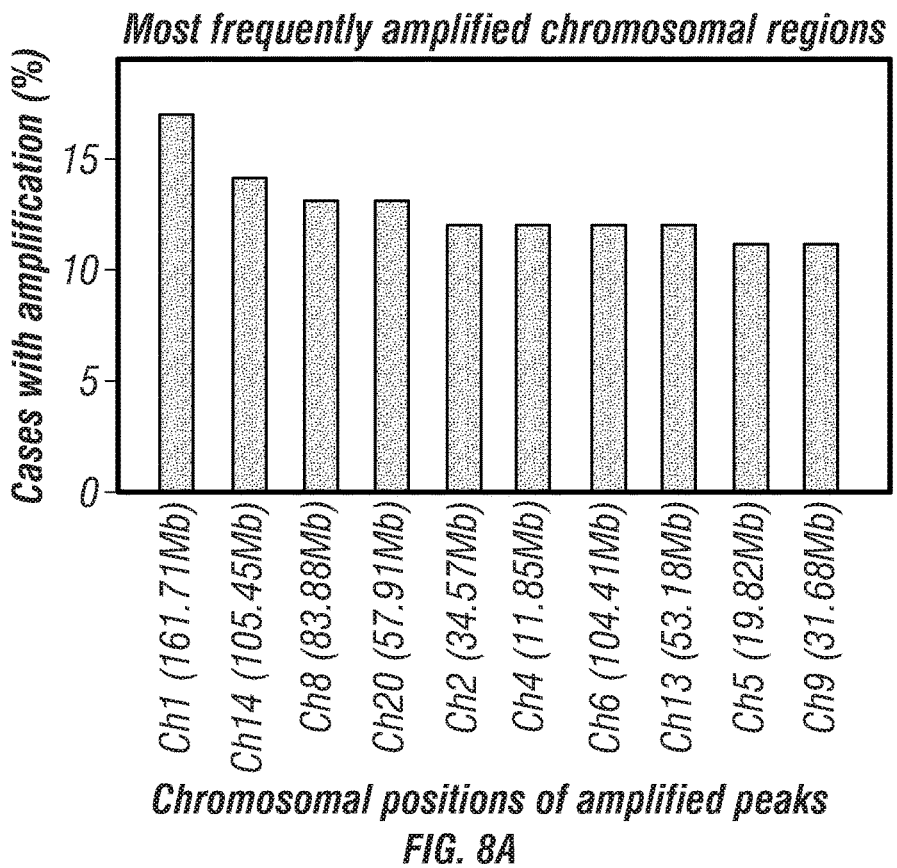
FIGS. 8A-8B: Copy number analysis of the MDACC cohort containing paired tumor samples and peripheral blood DNA from 14 patients with low-grade superficial (Ta-T1a) and high grade invasive urothelial carcinomas (T1b-higher) of the bladder (n=40).
Figure 8B:
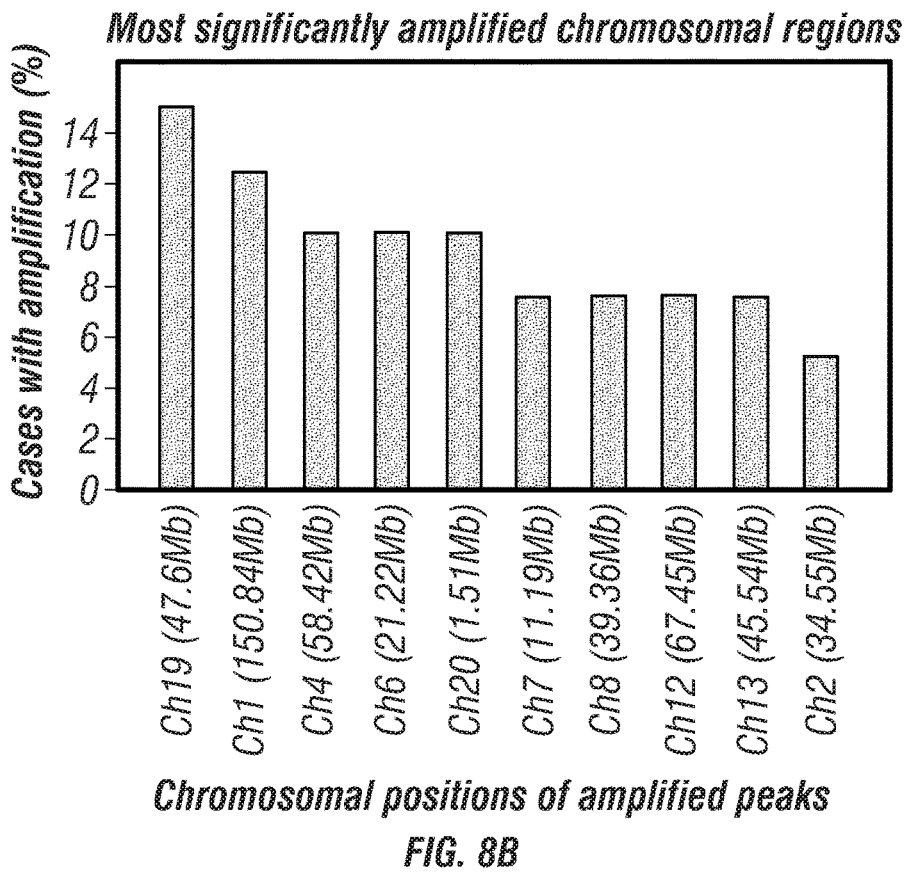
Figure 9:
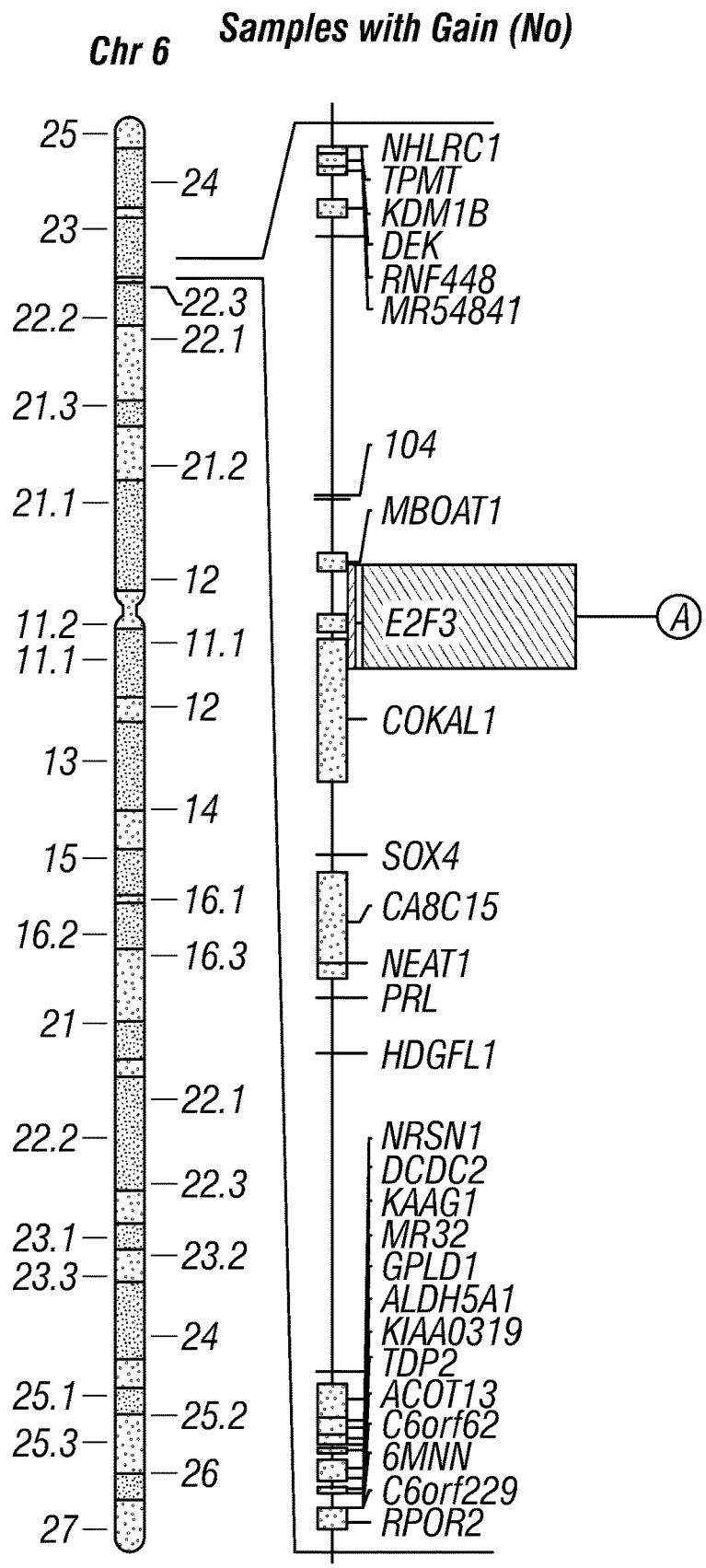
FIG. 9: Amplification patterns and genomic content of four chromosomal segments selected for the design of the Quartet Test.
Figure 9:
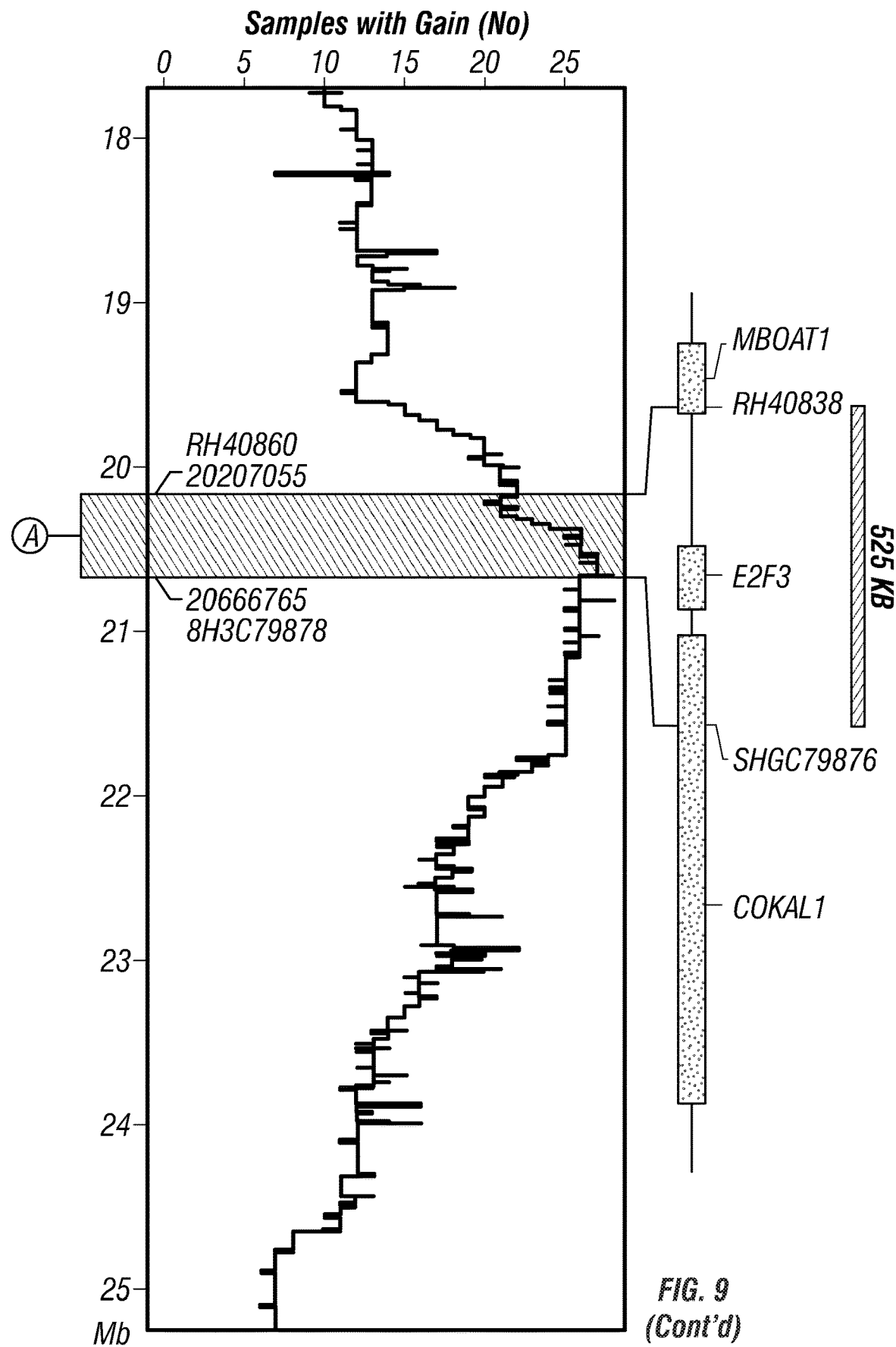
Figure 9:
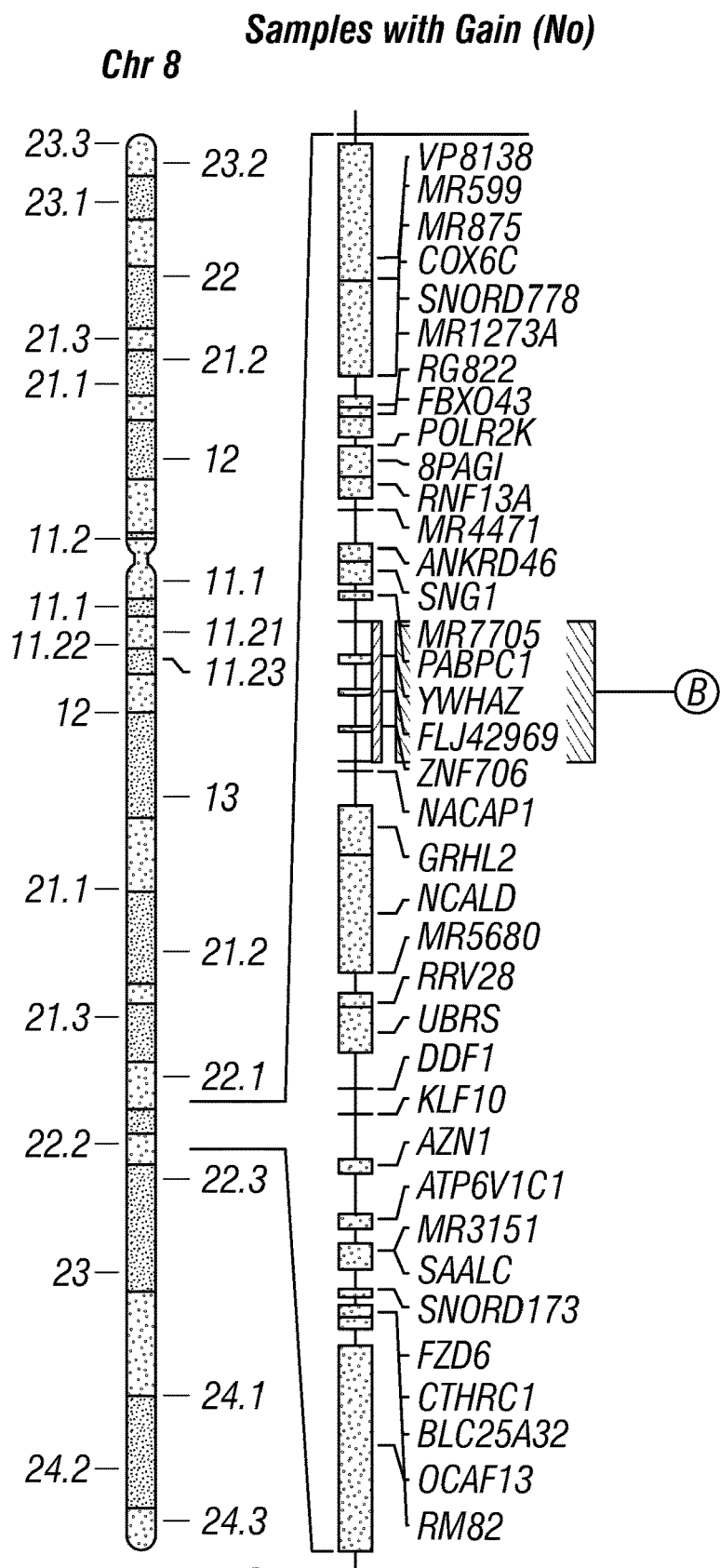
Figure 9:
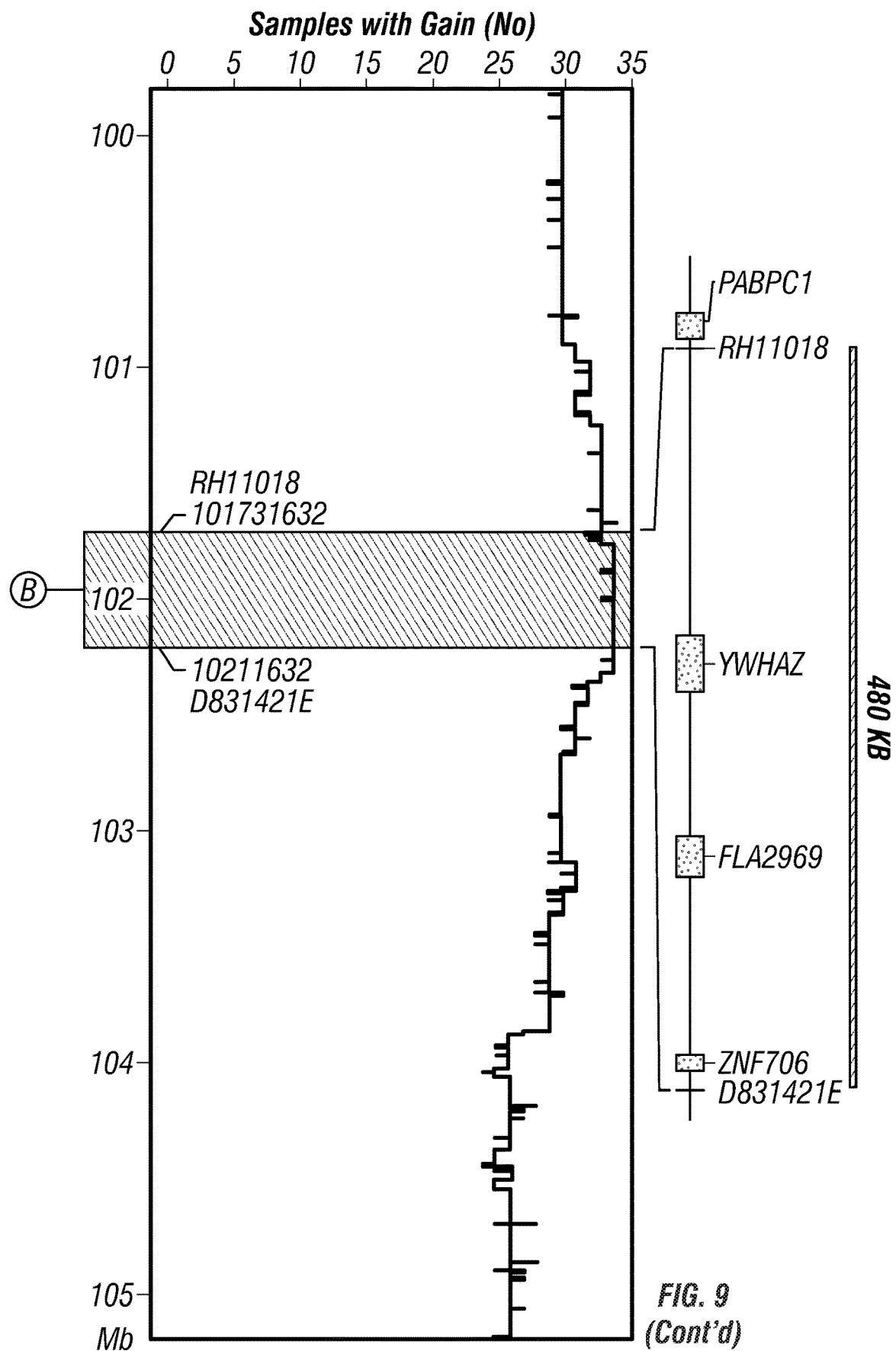
Figure 9:
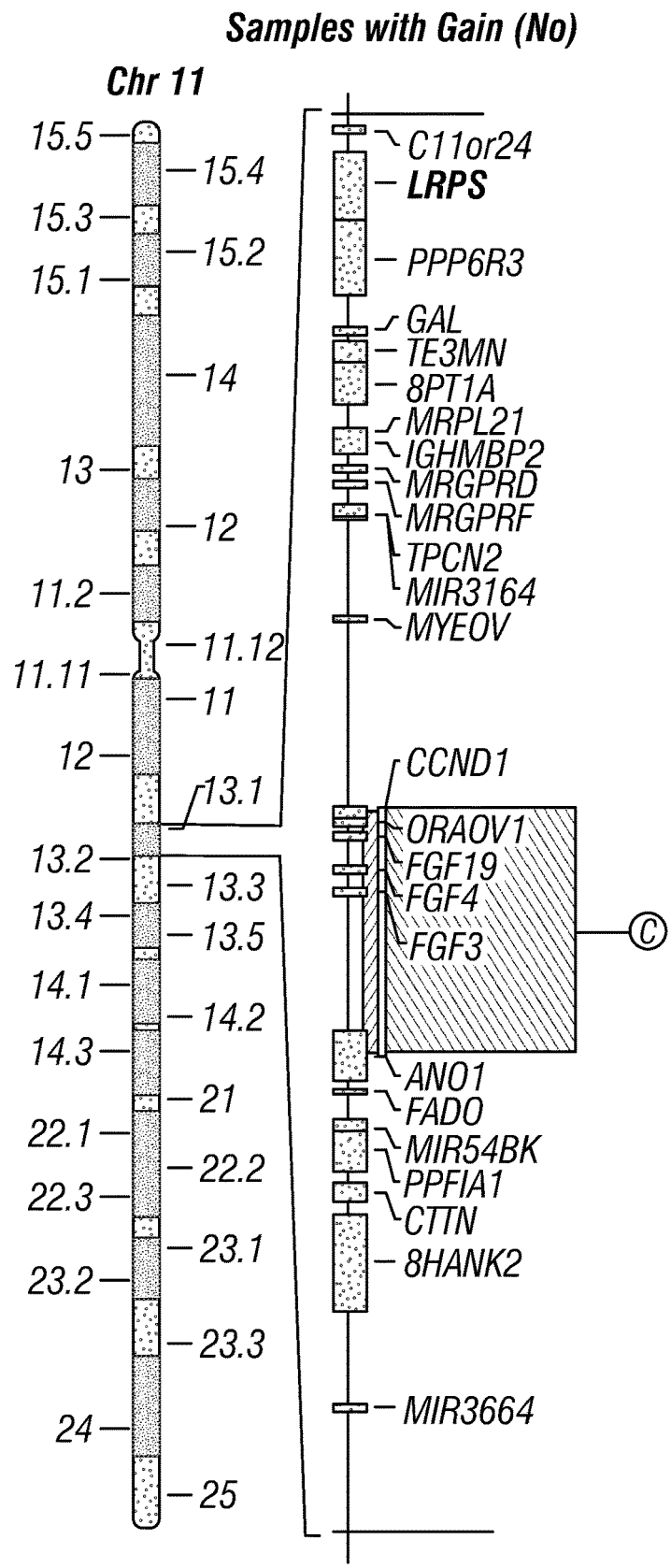
Figure 9:
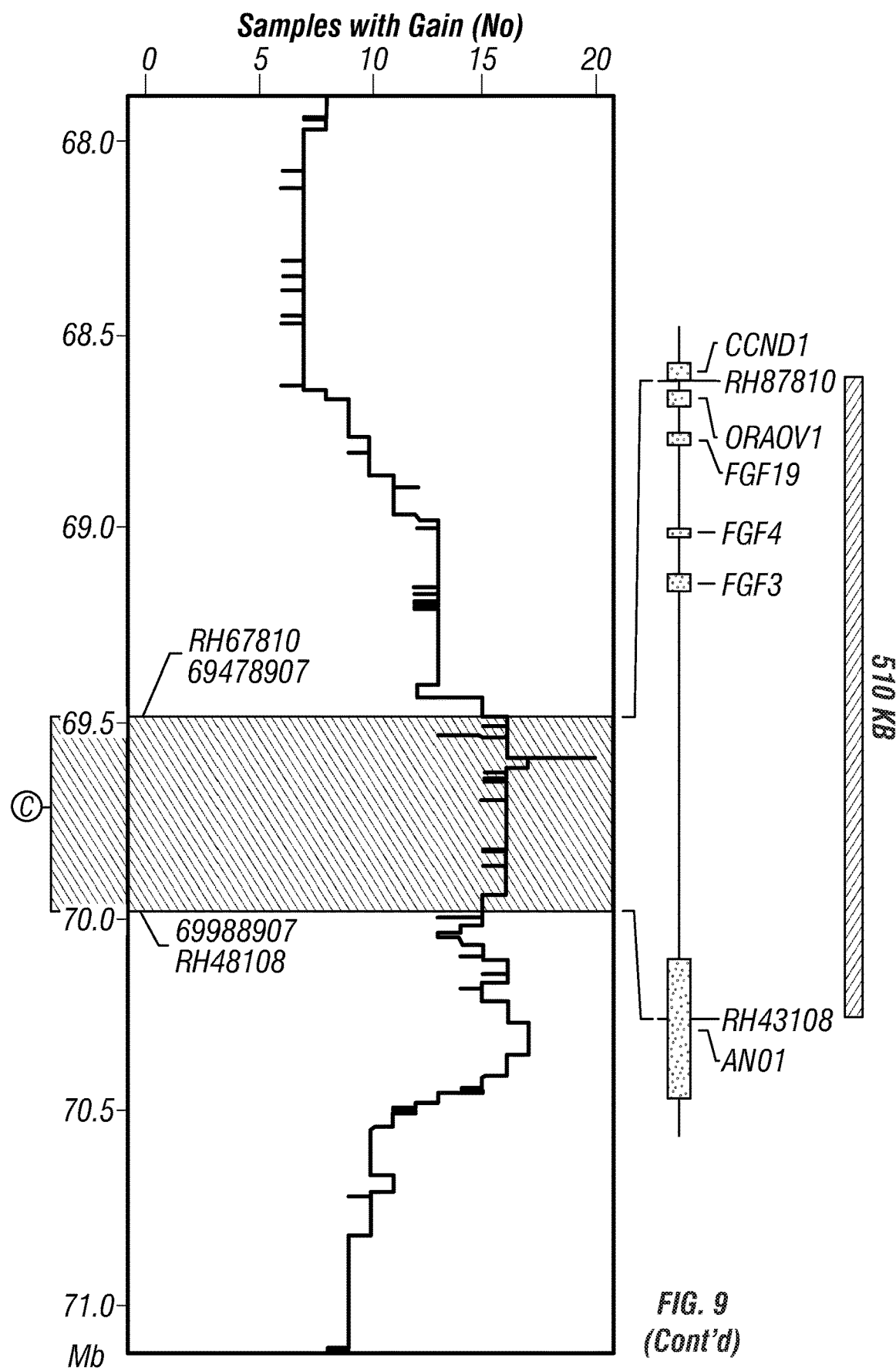
Figure 9:
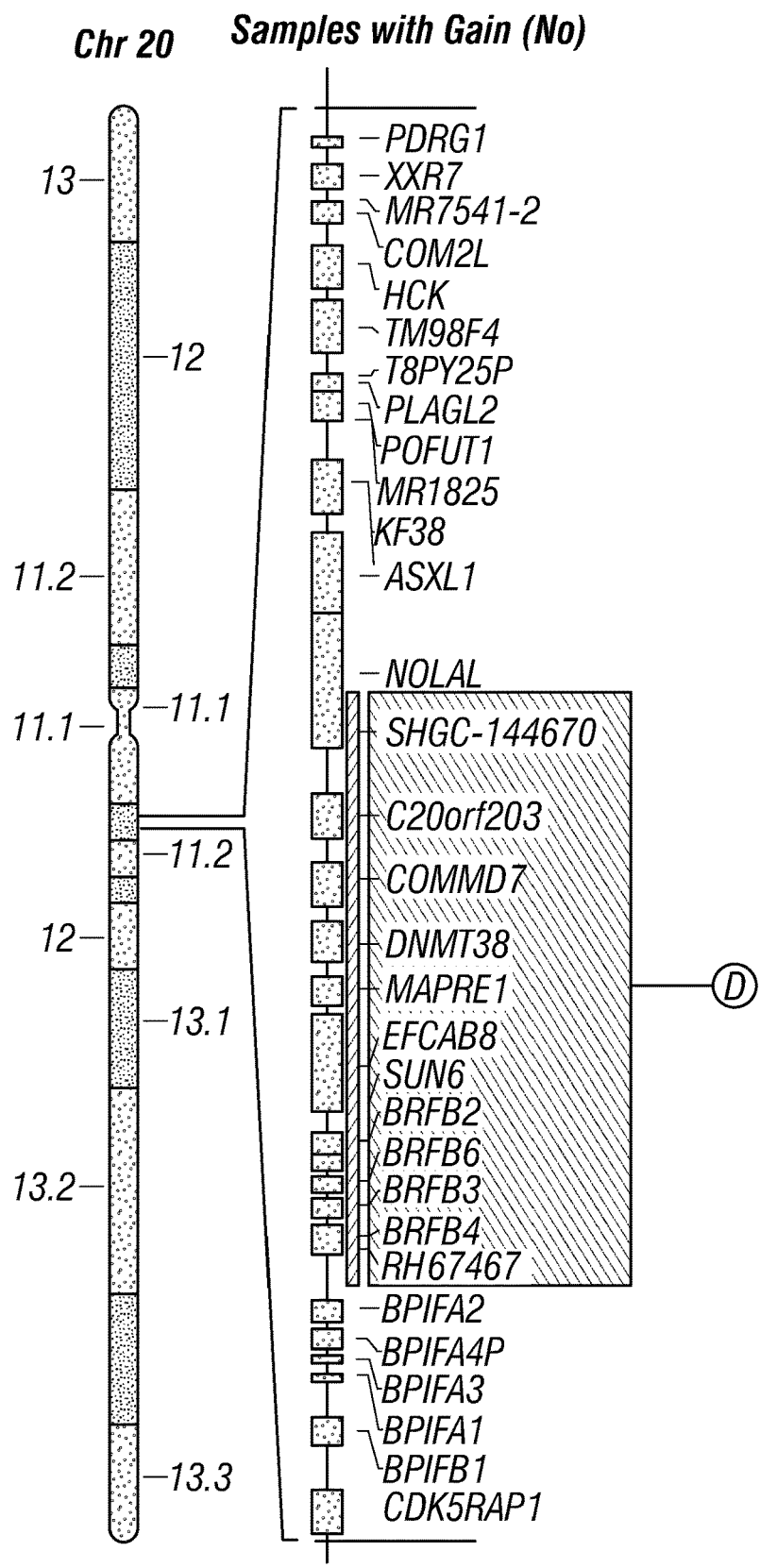
Figure 9:
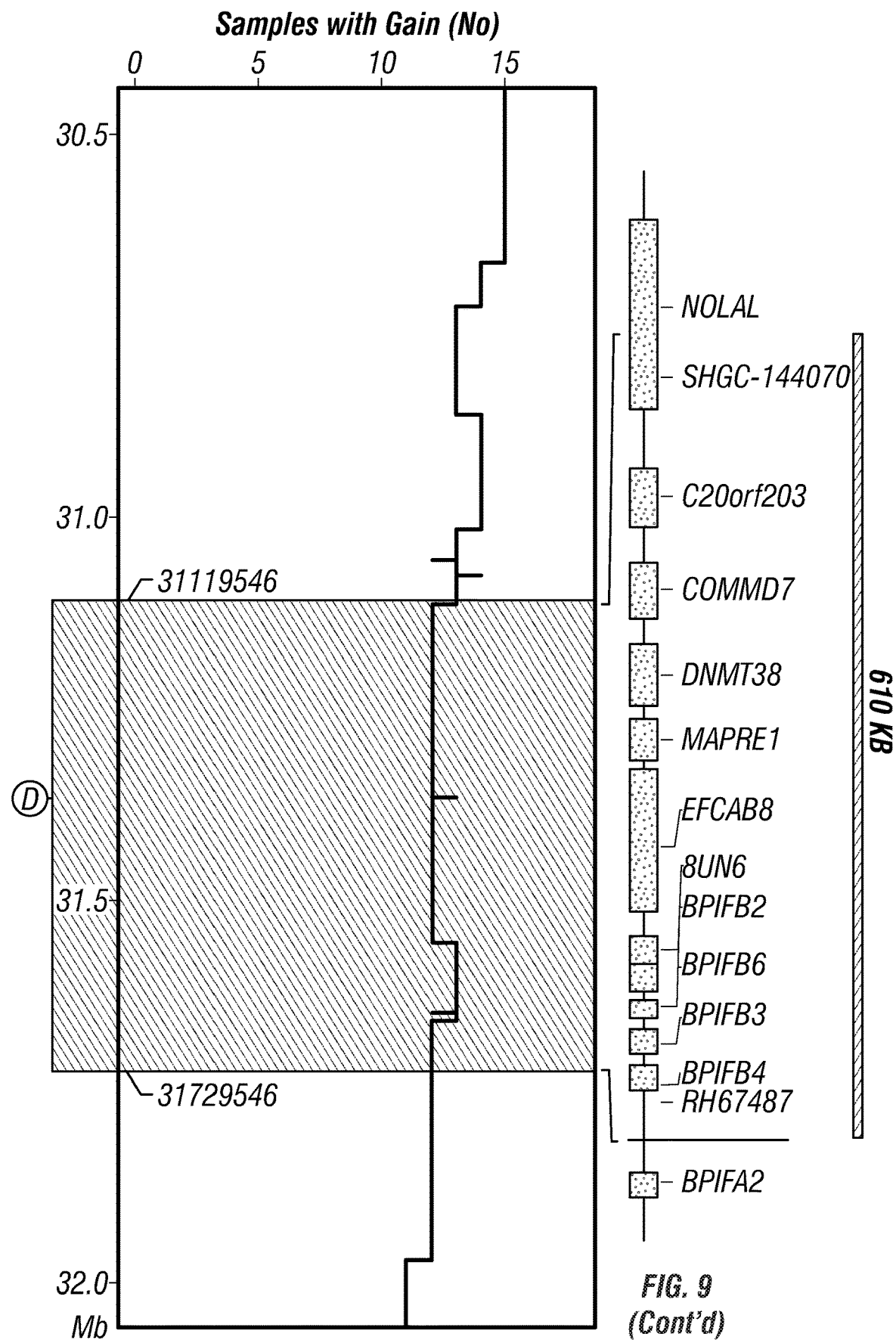

Copy number variation analysis and probe design. The overall plan of probe identification, design, and testing is outlined in FIG. 1. The purpose of the copy number analysis was to identify the most frequently amplified (regions scored 1 or 2 in the Genome Studio output) and markedly amplified (regions scored 2) chromosomal regions in order to design a multicolor FISH test. The goal of these analyses was to select the possibly best four probes. The number of probes was restricted to four because there were four commercially available fluorochromes that permitted their clear distinction at distinct wavelengths using a specific set of filters under a fluorescent microscope. Initial analysis of paired bladder tumor and peripheral blood samples from 40 cancer patients, 14 with superficial LGPUC (Ta-T1a) disease and 26 with invasive HGUC (T1b-higher) disease, identified the 10 most frequently and the 10 most markedly amplified chromosomal regions (FIGS. 2A, 8A and B). These most frequently and markedly amplified regions were validated on 129 tumor samples from the original published TCGA cohort (FIGS. 2B and C). These two sets of analyses were somewhat overlapping but not identical. In general, the positions of amplified peaks were virtually identical in both cohorts but the relative frequencies of amplification were different. Using these data, four chromosomal regions were selected to design the probes for the Quartet Test. These regions included amplified chromosomal segments showing distinct frequency peaks on chromosomes 6, 8, 11, and 20 (FIG. 2D). The specific chromosomal positions, their target genes, and the labeling fluorochromes included 6p22, E2F3—CDKAL1, 525 KB, green, Platinum Bright™495; 8q22. PABPC1-ZNF706, 480 KB, gold, Platinum Bright™530; 11q13, FGF19-FGF3, dark red, Platinum Bright™590; and 20q11.2, MAPRE1, 610 KB, blue, Platinum Bright™415 (FIG. 3). The specificity of the probes was initially tested both individually and in mixture on normal human metaphase cells which showed that all FISH probes specifically hybridized to their respective chromosomal loci (FIGS. 3A and B). A mixture of the four probes generated the expected diploid eight signals for their respective fluorescent tags in normal peripheral blood lymphocytes and urothelial cells (FIG. 3C). Preliminary testing on touch prints from high grade bladder carcinoma samples revealed gross aneuploidy with multiple (more than 2) copy numbers for all probes in practically all tumor cells (FIG. 3D).

Quartet Test Study in Voided Urine. The performance of the Quartet Test was initially analyzed on paired samples of voided urine typically collected 2-3 days before cystoscopy and tumor tissue from a cohort of 53 patients: 19 patients with LGPUC and 34 patients with HGUC (FIGS. 4A-D). In every instance, abnormal copy number levels were detected in touch print preparations of the tumor tissue and the corresponding paired voided urine samples from the same patient. Although there were some discrepancies, in the majority of cases the percentage of cells with abnormal copy numbers for one or more FISH probes were similar in tumor and urine samples from the same patient. It was also evident that the proportions of cells with abnormal copy number in both tumor and voided urine samples were significantly higher in HGUC than in LGPUC.

Figure 10:
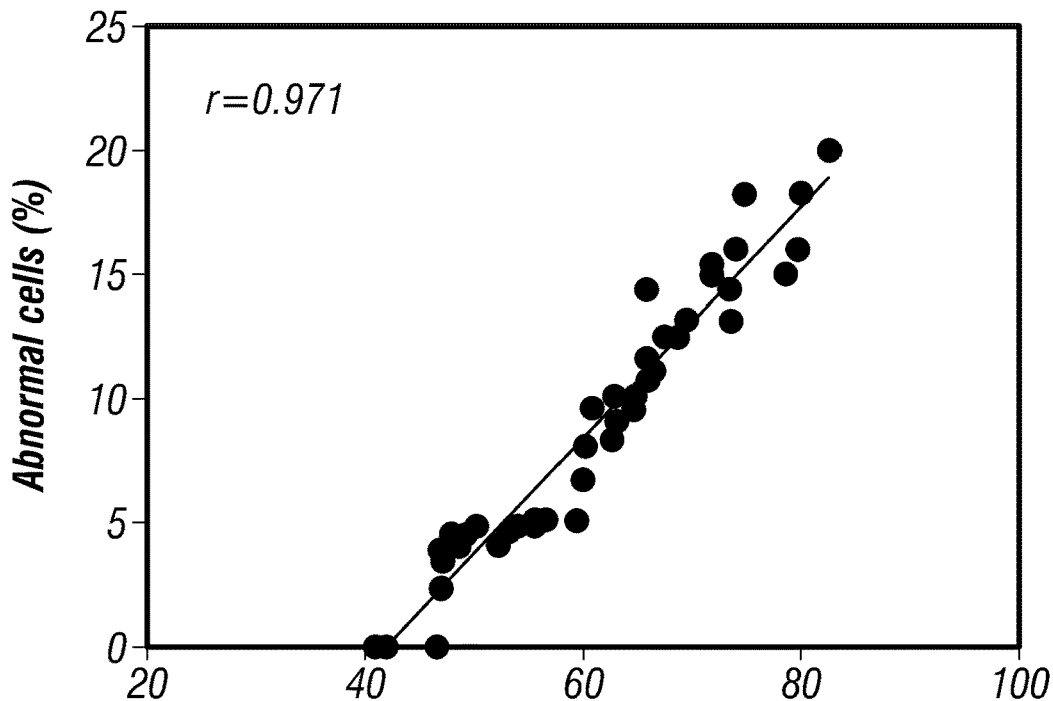
FIG. 10: Proportion of abnormal cells in voided urine in the control groups (n=48). Scatter plot analysis of percentage of abnormal cells in voided urine in relation to age (Pearson correlation coefficient, r=0.971).

The performance of the Quartet Test was then evaluated in a blinded fashion in voided urine samples from 98 patients with bladder tumors and 48 controls (FIGS. 5A-D). Only samples that contained at least 10 intact cells with measurable, clearly defined fluorescent signals, were used but in the majority of cases the number of analyzed cells was 20 or more. A small fraction of samples could not be analyzed because of an insufficient number of intact cells with fluorescent signals available for microscopic inspection in cytologic preparations of urine sediments (14.5% of samples in control group and 7.1% of samples in the cancer group). The initial analysis of the control samples disclosed that the majority of them contained a small fraction of cells with an increased copy number of individual probes. They typically involved extra numeral signal in a range of 3-4 copies restricted to one probe. The extra numeral copy signals involving two and four probes were present only in two cases of the control group. The AP value in the control group ranged from 2 to 20% (8.69±5.33%) and strongly correlated with age (r=0.971) (FIG. 10). It was significantly higher (p=0.002) in males (10.8±5.6%) when compared to females (6.1±3.7%).

Figure 6A:
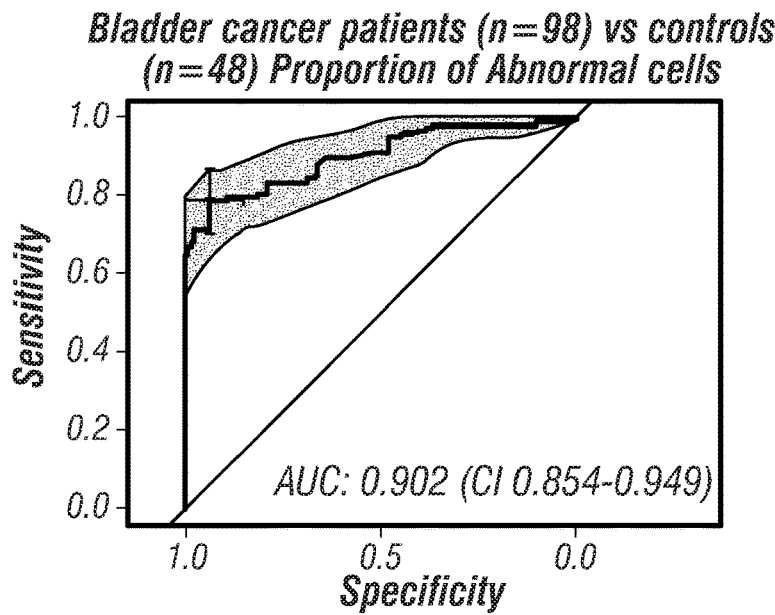
FIGS. 6A-6F: Detection of bladder cancer in voided urine by the Quartet Test (n=146).
Figure 6B:
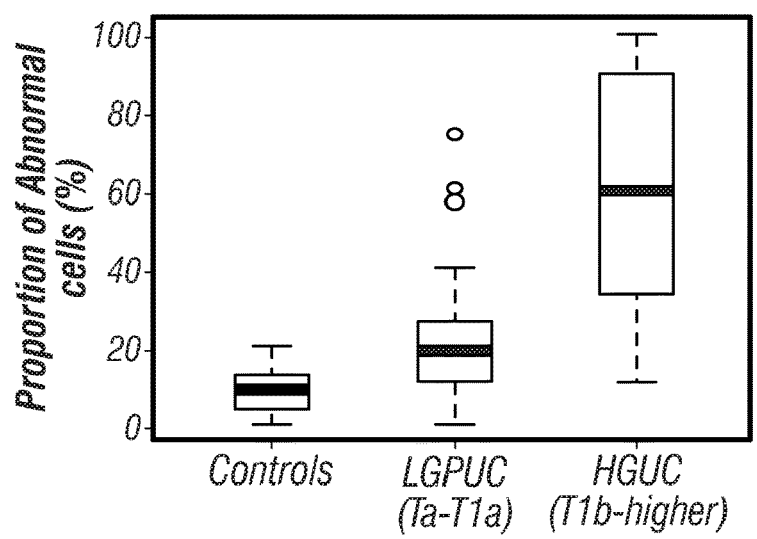

By analyzing the ROC curve for the AP score (FIG. 6A), the optimal cutoff score was identified as being 0.16. Samples in which >16.4% of the cells examined contained at least one probe with three or more copies were flagged as likely having bladder cancer. With these criteria, the AP Quartet Test was positive for 77/98 samples of patients with bladder cancer, corresponding to a sensitivity of 78.6% (approximate 95% coverage interval 0.694, 0.855). The AP Quartet Test was positive for 3/48 control samples, corresponding to a specificity of 93.8% (0.831, 0.977). The area under the ROC curve (AUC) is 0.902 (95% CI=0.855 to 0.949; P<0.001) (FIG. 6A). Overall, the proportion of cells with abnormal copy number was significantly higher (p<0.001) in high grade tumors (61.20±28.46) when compared to low grade tumors (21.72±14.48) and benign controls (8.69±5.33) (FIG. 6B).

There were striking differences in the degree of amplification among high and low grade tumors as well as benign controls. The proportion of cells with a low degree of amplification (three to four copies for at least one probe) was significantly higher in high grade tumors (27.11±16.74) when compared to low grade tumors (19.32±12.91) and benign controls (8.61±5.31).

Figure 6C:
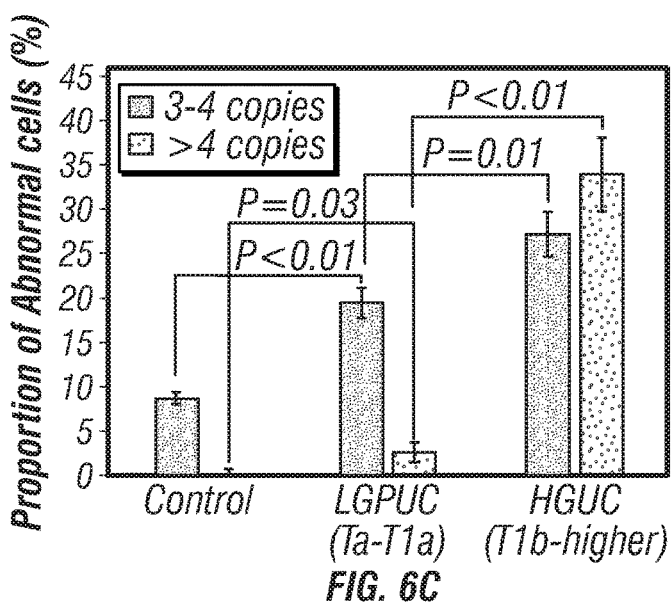
Figure 6D:
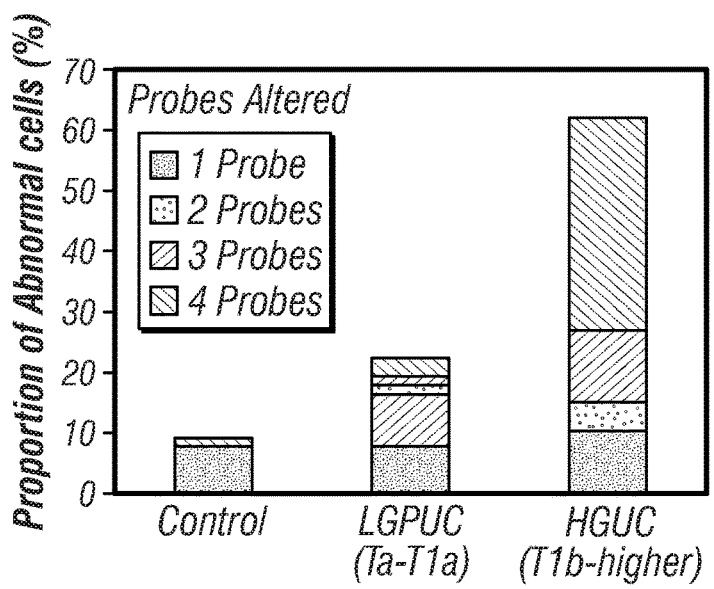
Figure 6E:
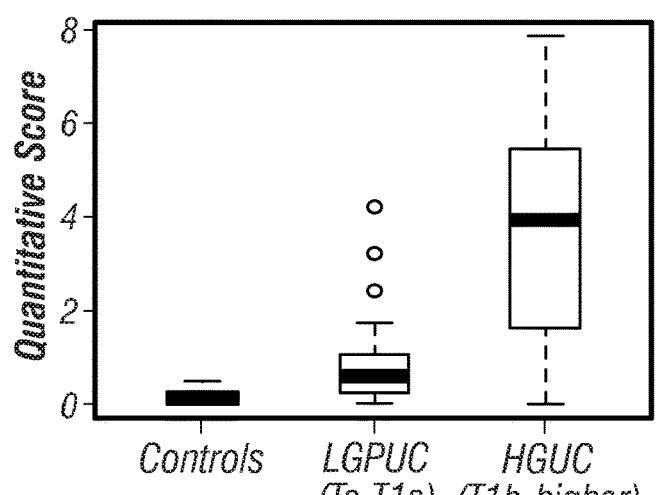
Figure 6F:
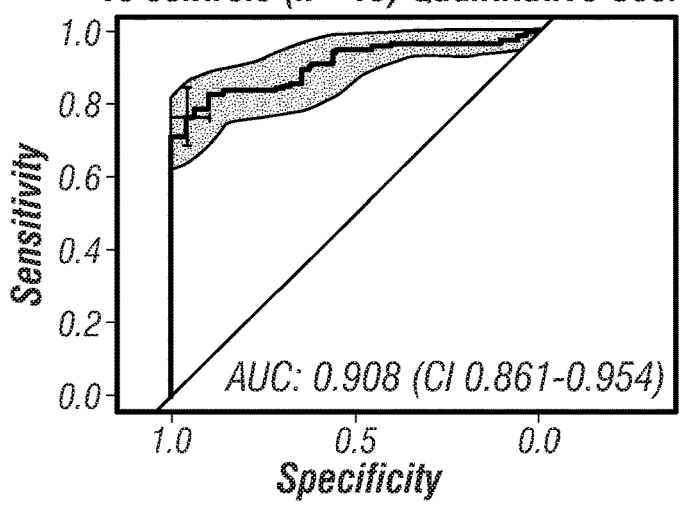

There were striking differences among the proportions of cells with a high degree of amplification (greater than four copies for at least one probe) in high grade tumors (34.02±29.48) when compared to low grade tumors (2.4±7) (FIG. 6C). Urothelial cells in voided urine samples from benign controls had virtually no cells with more than four copies for any of the probes. A similar pattern of changes was observed when the proportions of cells with large numbers of altered probes were analyzed (FIG. 6D). High grade tumors were characterized by large populations of cells which showed increased copy numbers for more than two probes. In fact, on average, more than 80% of the cells in these tumors showed alterations of all four probes. These data suggest that a pattern of amplifications detected by the four probes in exfoliated cells from voided urine reflects the degree of increased copy numbers in the tested chromosomal loci of bladder cancer cells. In order to provide a quantitative assessment reflecting the degree of this change, a weighted QS was designed incorporating numbers of altered probes seen per cell as well as binary altered/unaltered calls. With the formula for QS described Example 2, the maximum score is 8. The QS values for high grade tumors (3.73±2.32) were strikingly higher for high grade tumors when compared to low grade tumors (0.77±0.76) and benign controls (0.14±0.13) (FIG. 6E). There was a minimal overlap of the QS values between high and low grade tumors. Examination of the ROC curve for the QS Quartet Test shows an optimal cutoff score of 0.41. Using this rule, the QS Quartet Test was positive for 75/98 samples of patients with bladder cancer, corresponding to a sensitivity of 76.5% (approximate 95% coverage interval 0.672, 0.838). The QS Quartet Test was positive for 2/48 control samples, corresponding to a specificity of 95.8% (0.860, 0.987). The area under the ROC curve (AUC) is 0.908 (95% CI=0.861 to 0.954; P<0.001) (FIG. 6F). The negative and positive predictive values of the Quartet Test were also assessed. The negative predictive value calculated using AP was 68.2% and for QS was 66.7%. The positive predictive value for AP was 96.3% and for QS was 97.4%.

Figure 5A:
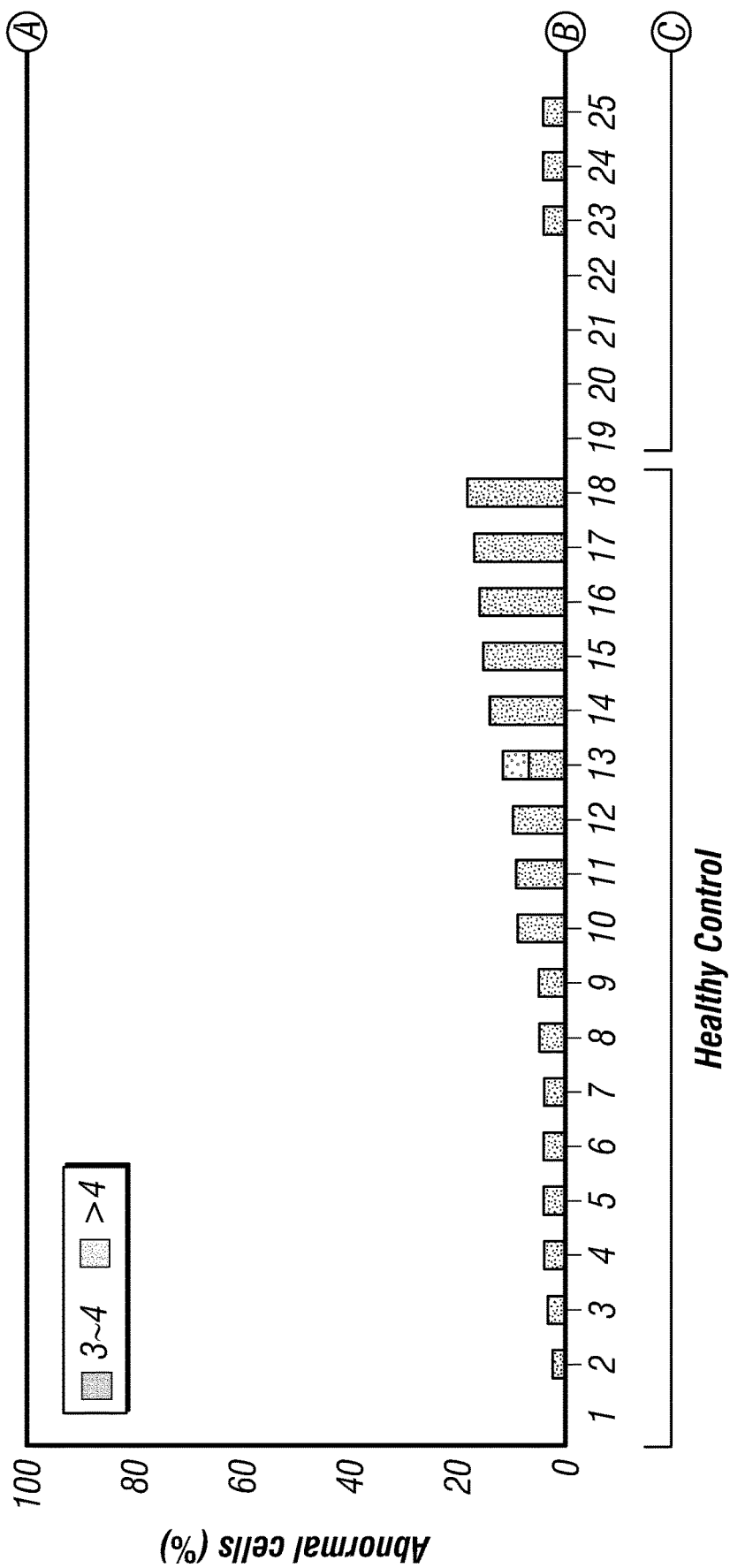
FIGS. 5A-5D: Quantitative assessment of cells with abnormal copy number by the Quartet Test in voided urine samples (n=146).
Figure 5A:
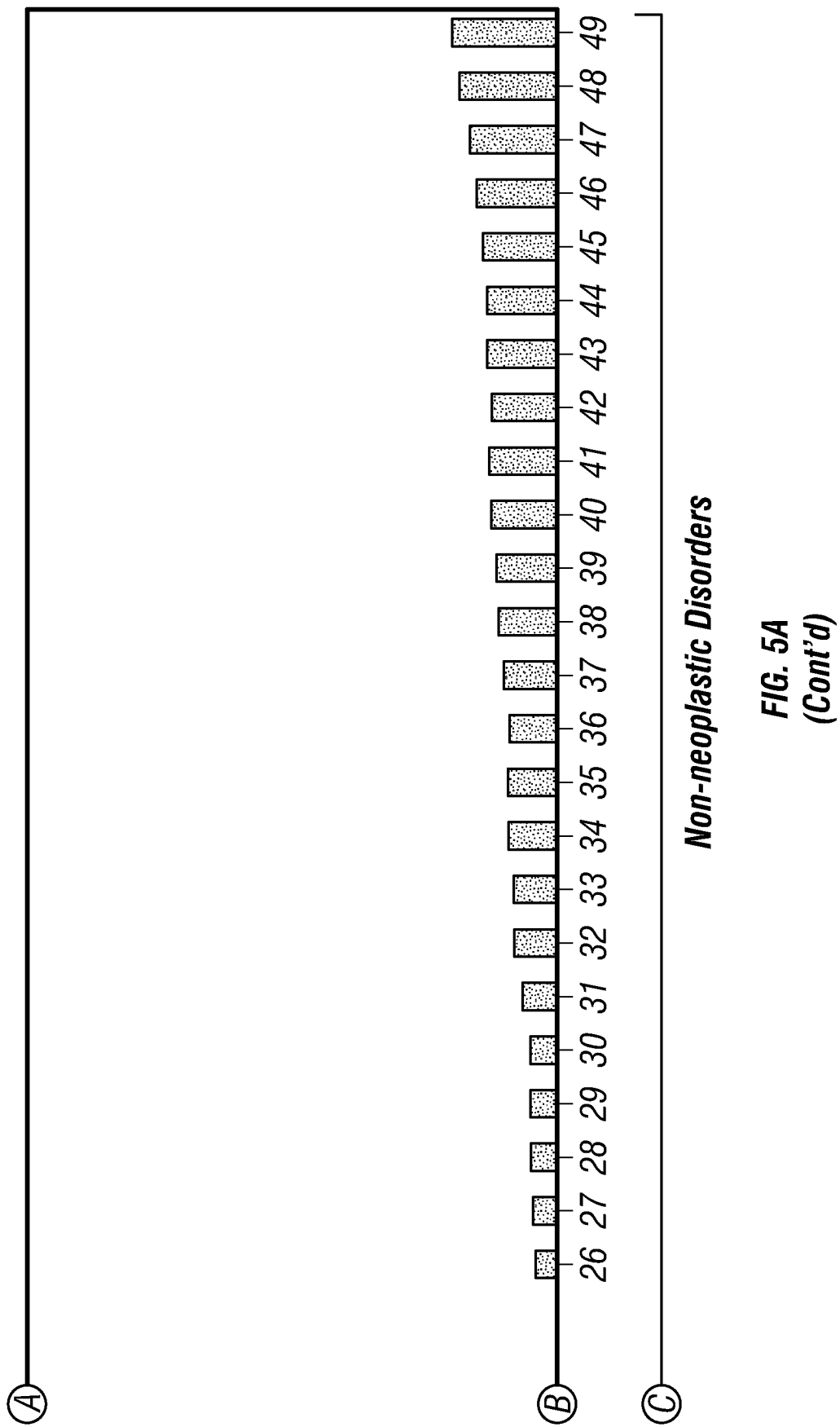
Figure 5B:
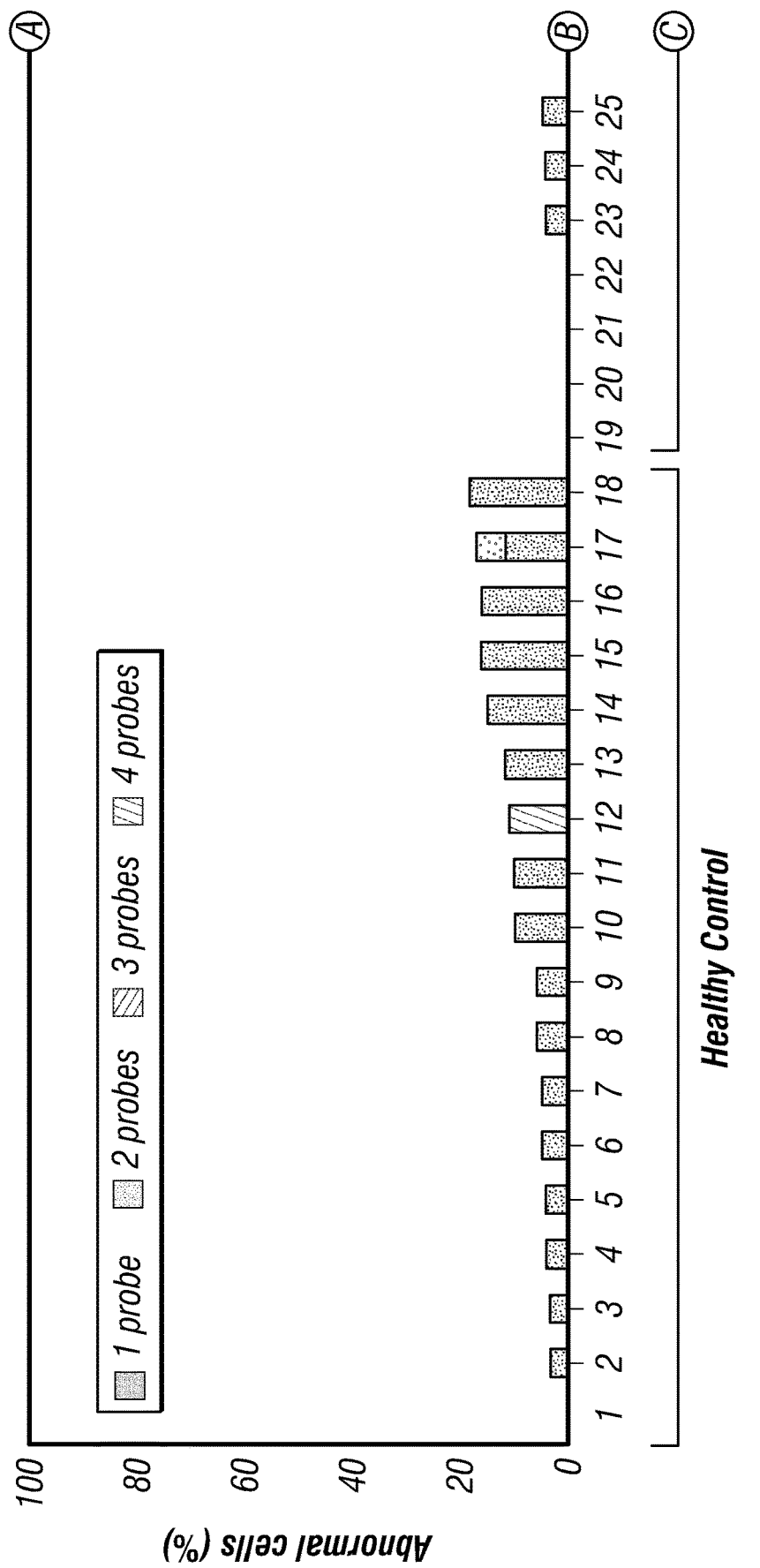
Figure 5B:
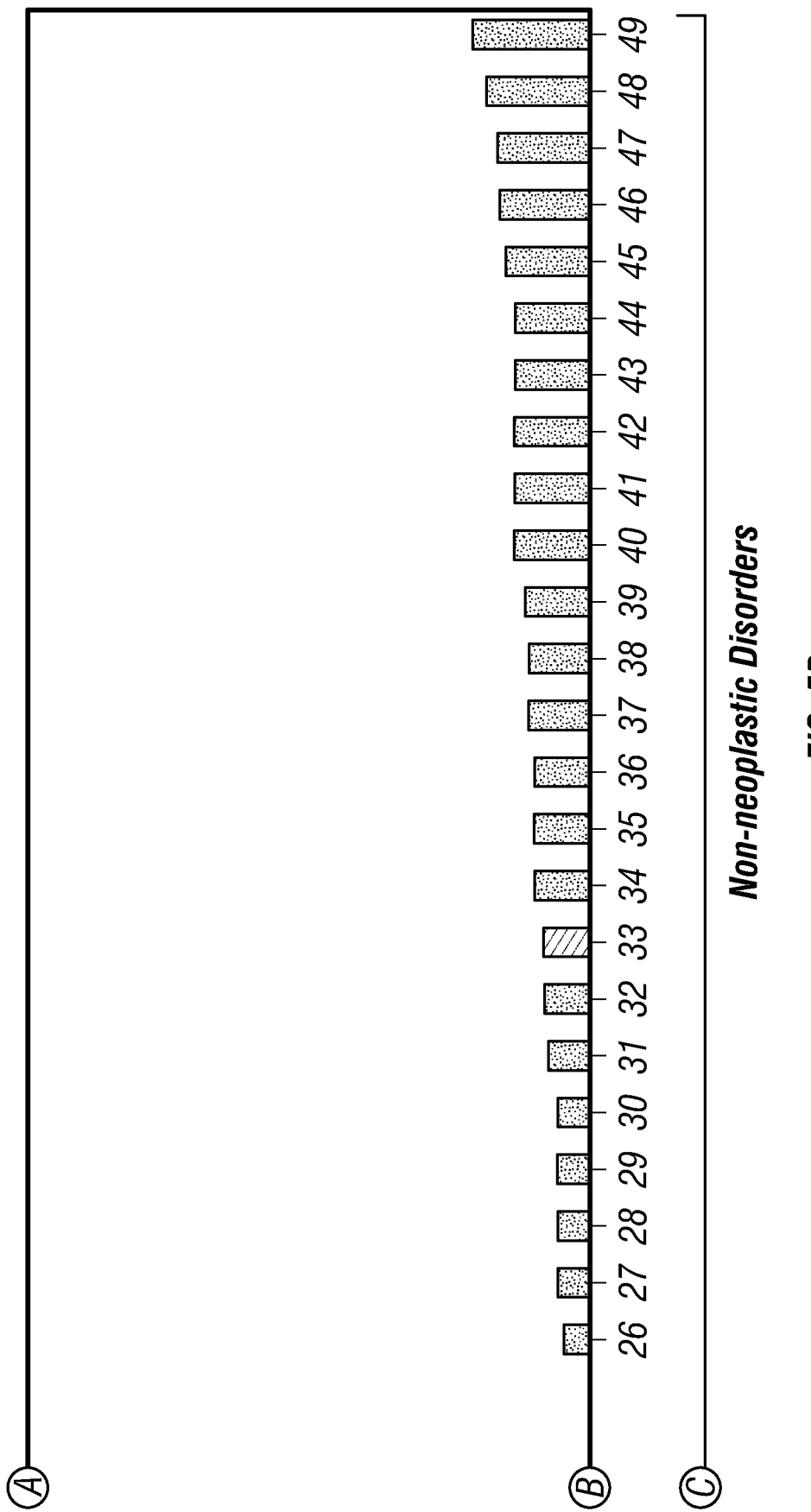
Figure 5C:
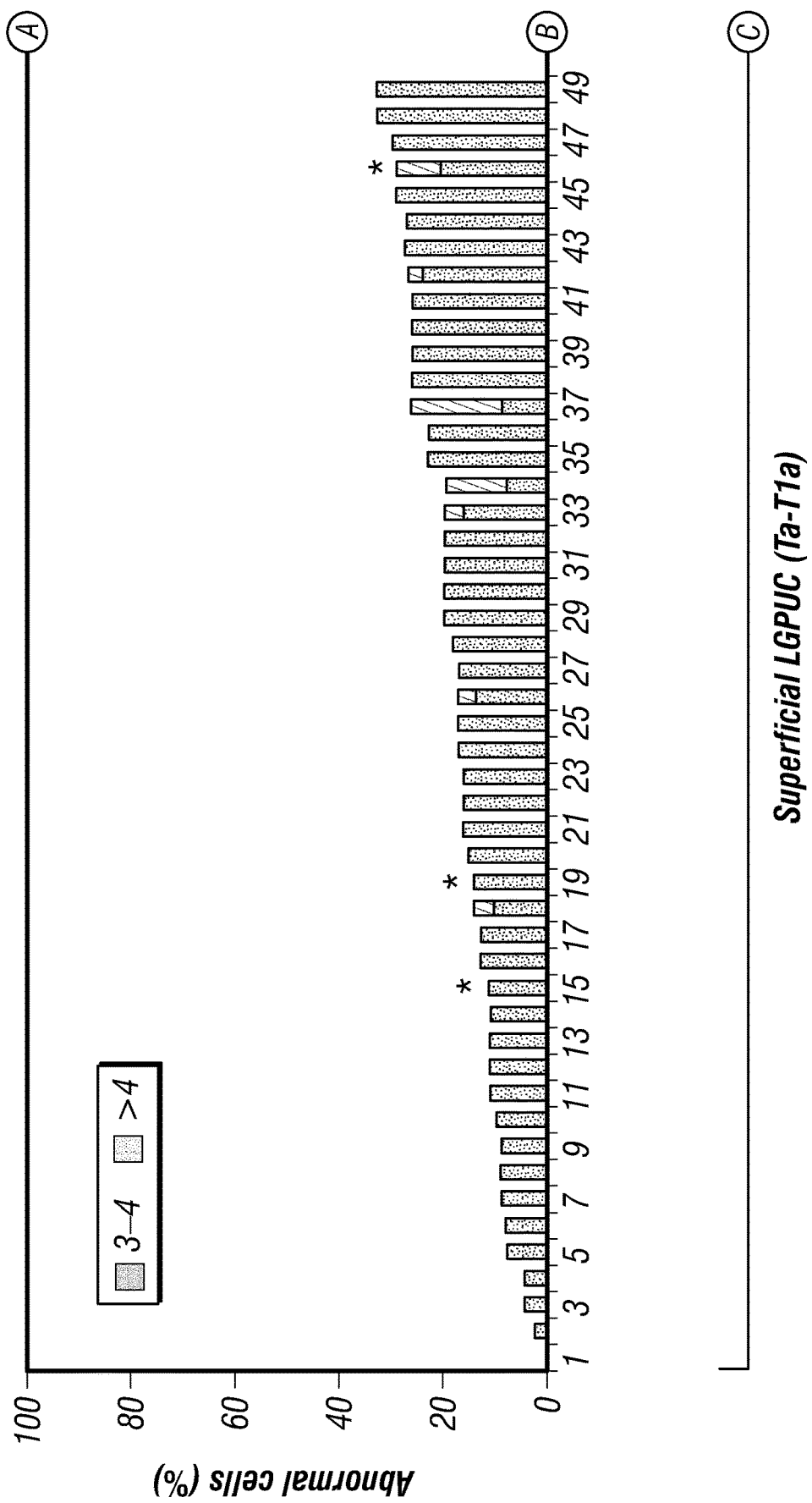
Figure 5D:
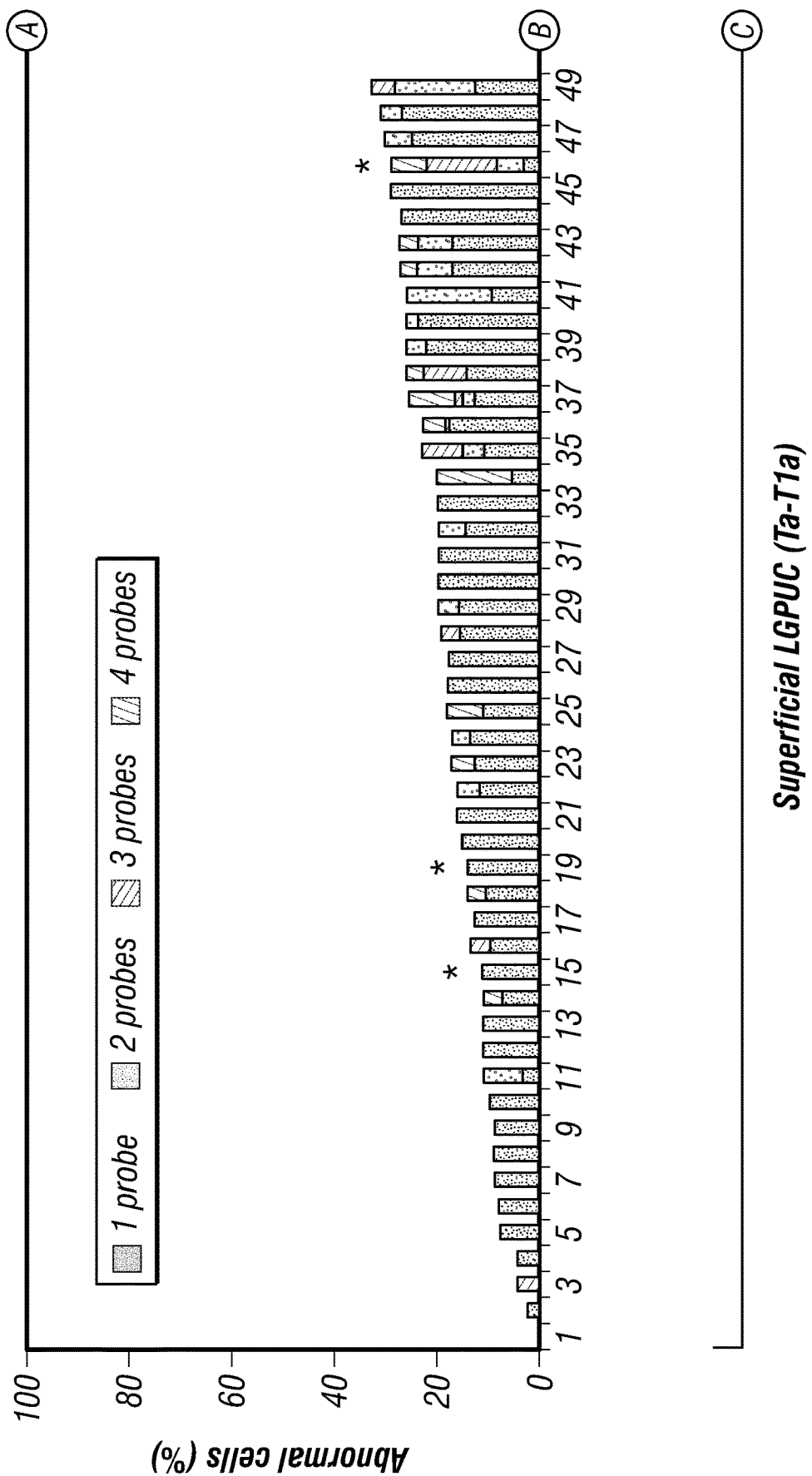
Figure 5D:
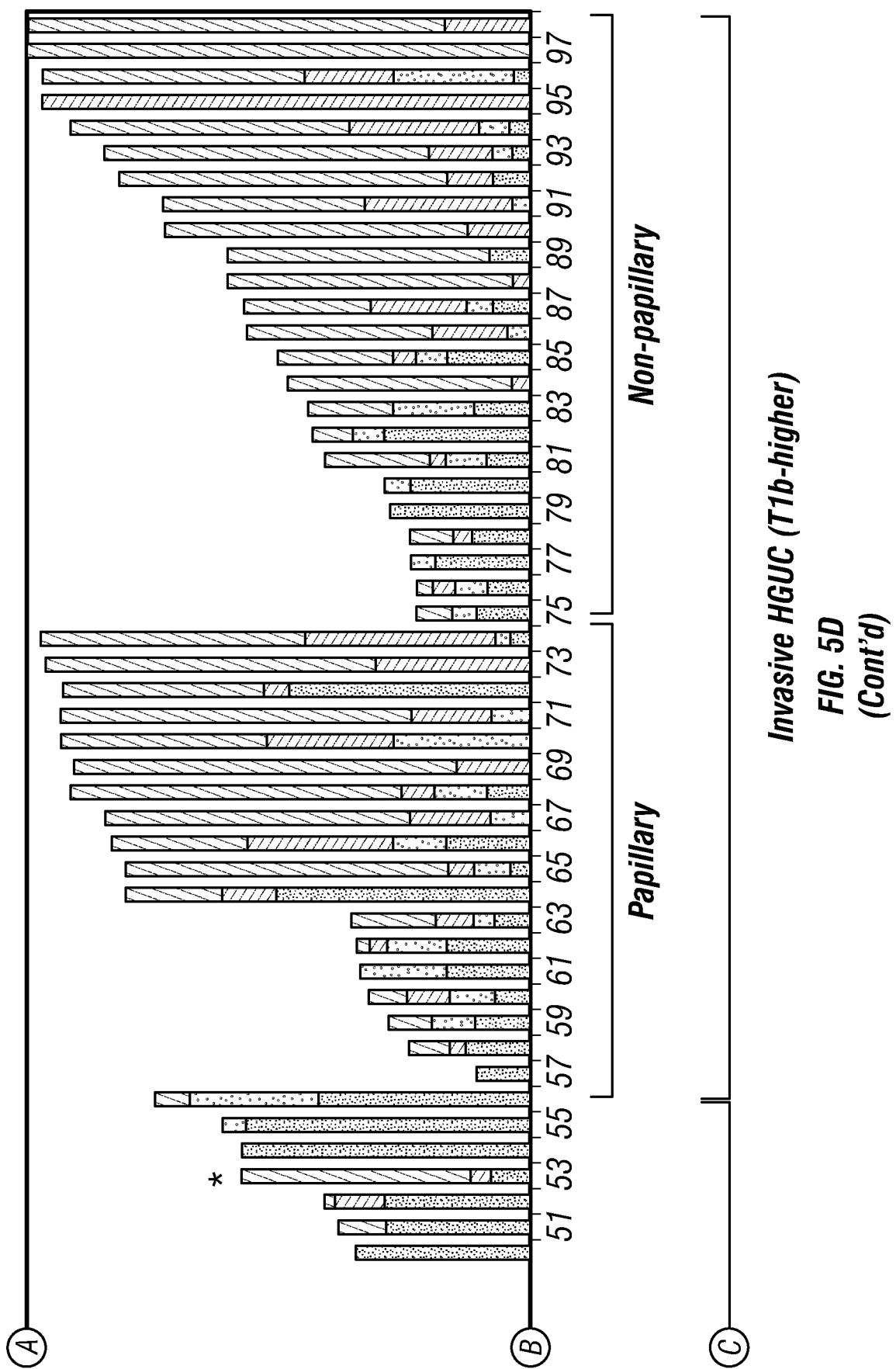
Figure 11A:
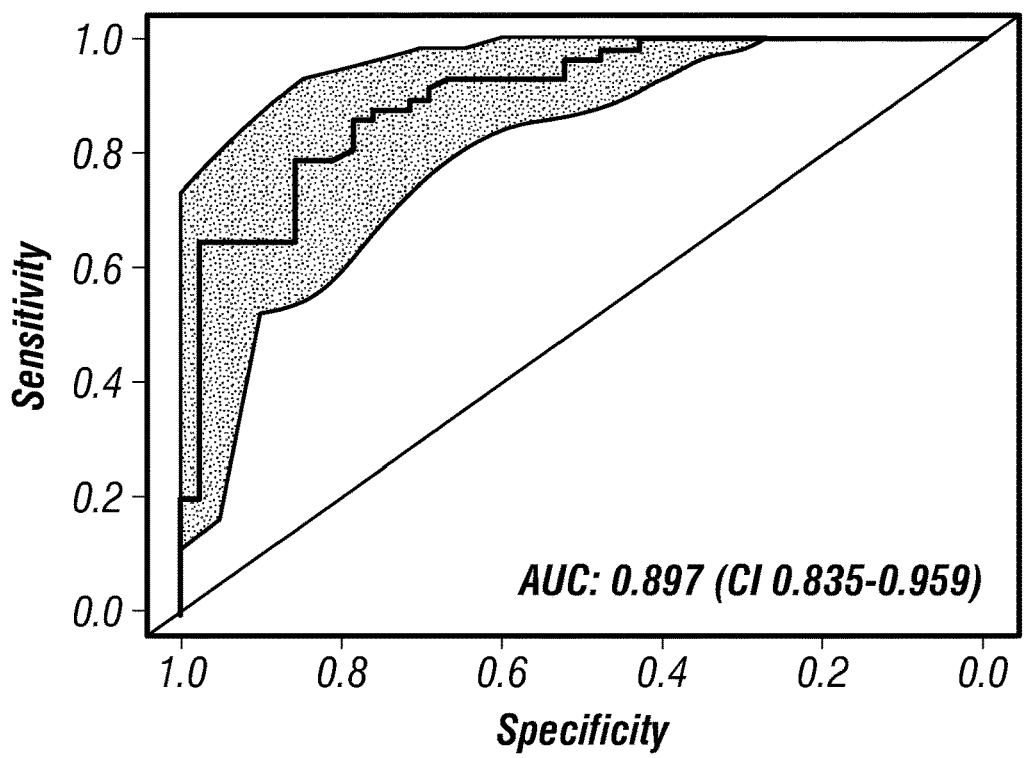
FIGS. 11A-11C: Assessment of bladder cancer grade by the Quartet Test.
Figure 11B:
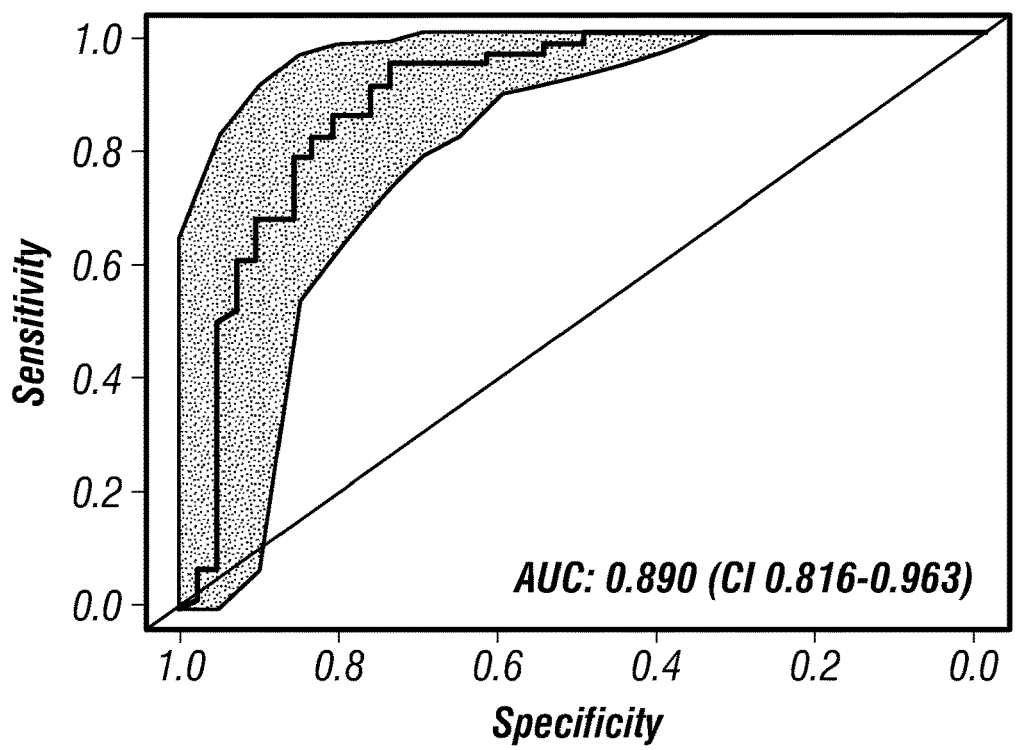
Figure 11C:
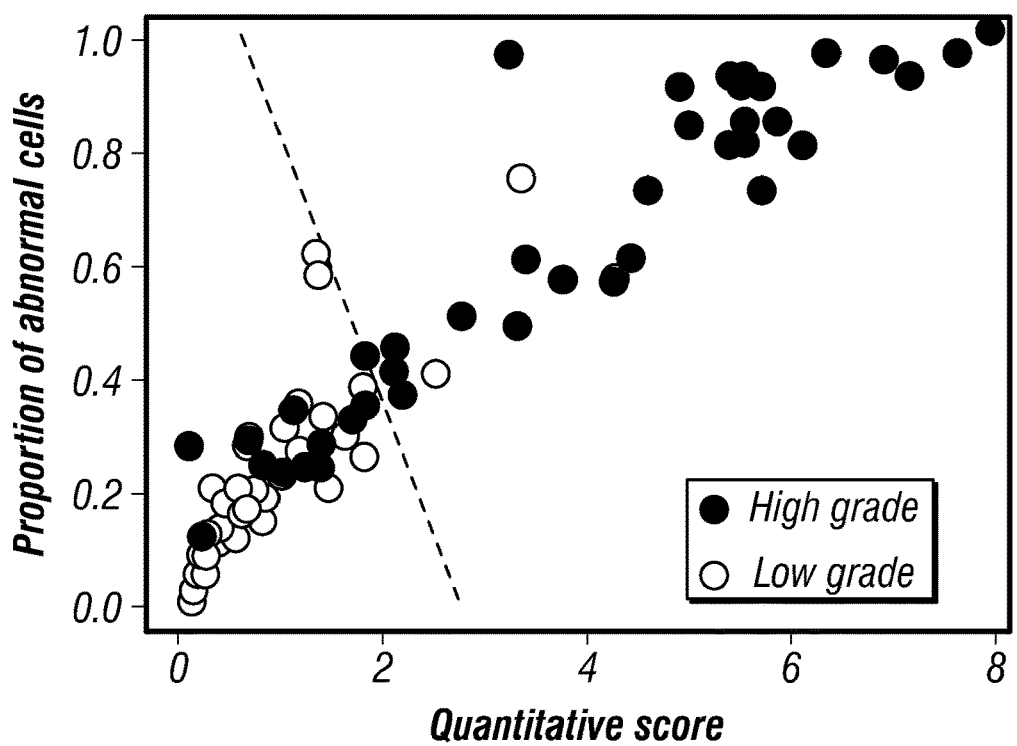
Figure 12A:
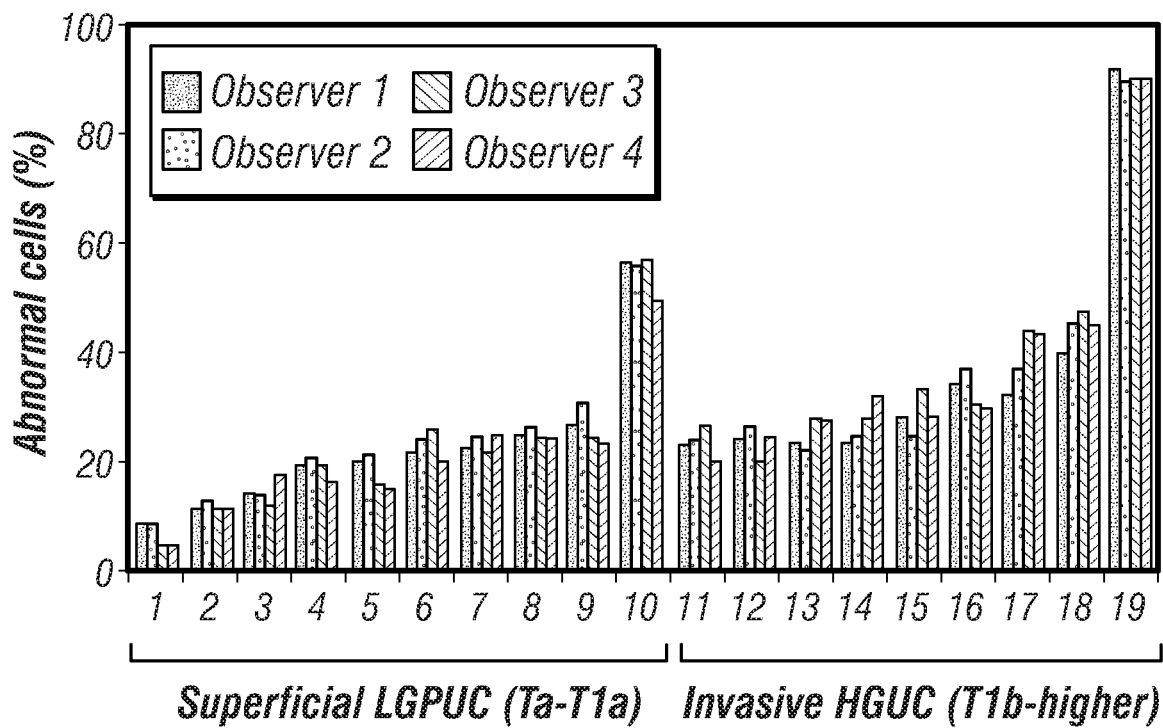
FIGS. 12A-12F: Interobserver variability (FIG. 12A) Proportion of abnormal cells in 19 cases of voided urine samples from patients with bladder cancer assessed by four independent observers.
Figure 12B:
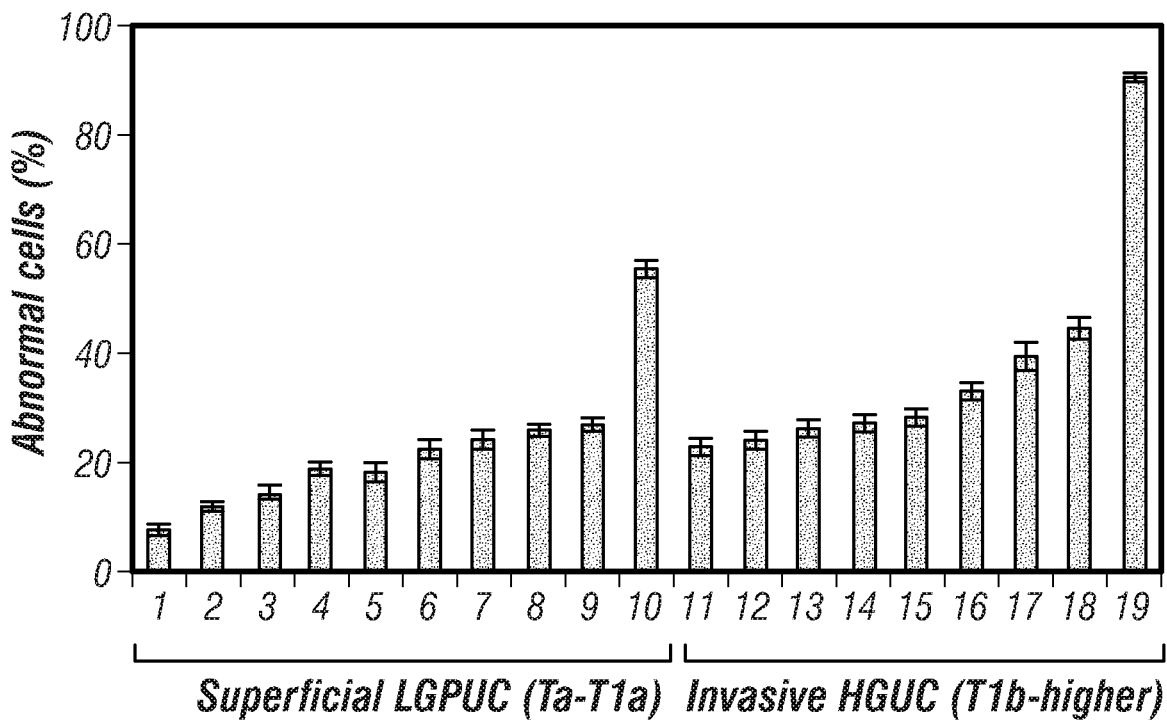
Figure 12C:
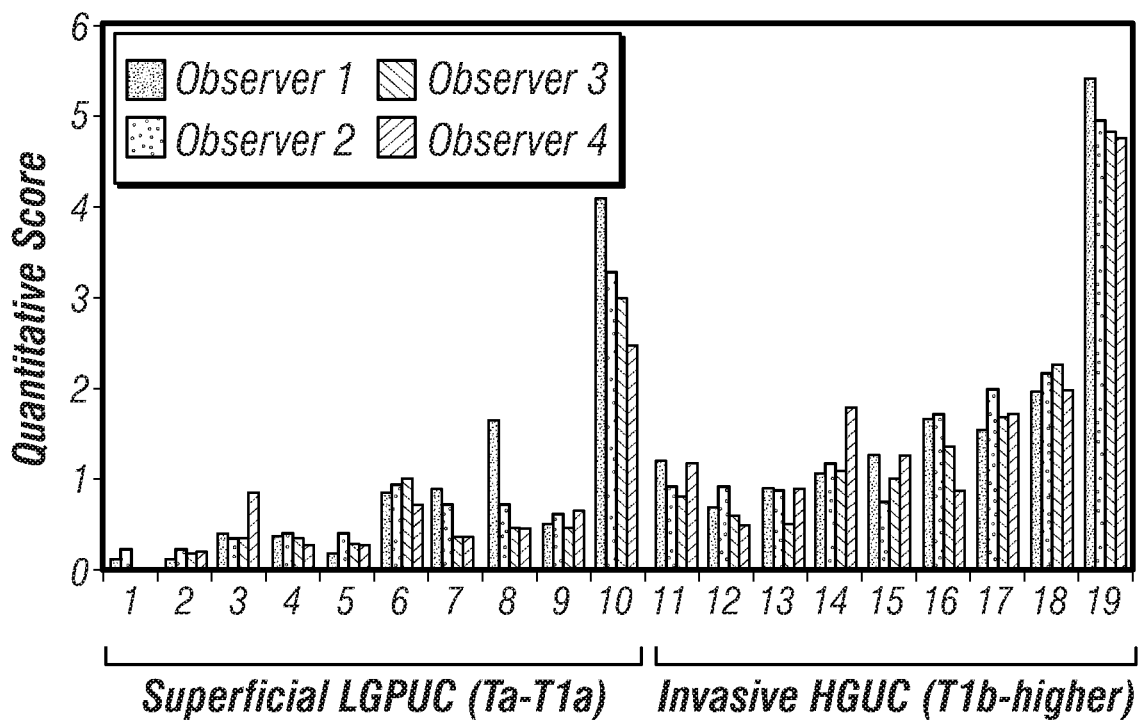
Figure 12D:
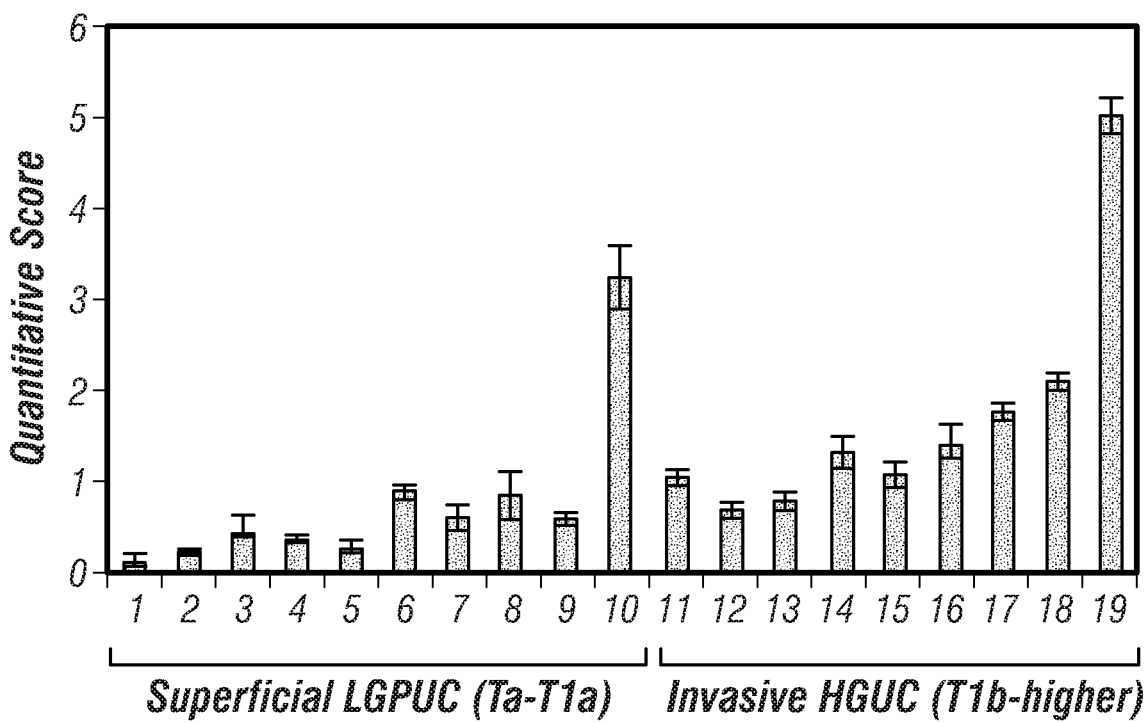
Figure 12E:
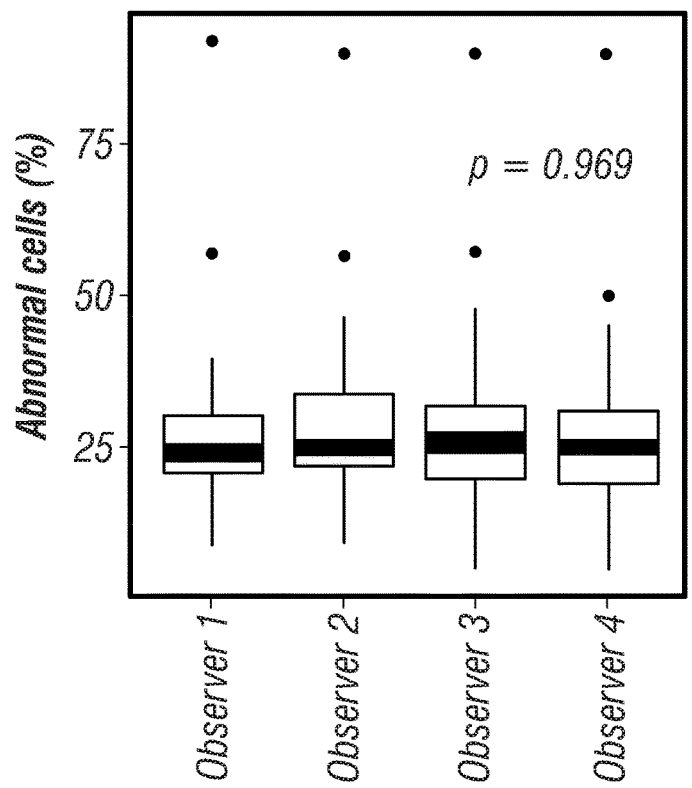
Figure 12F:
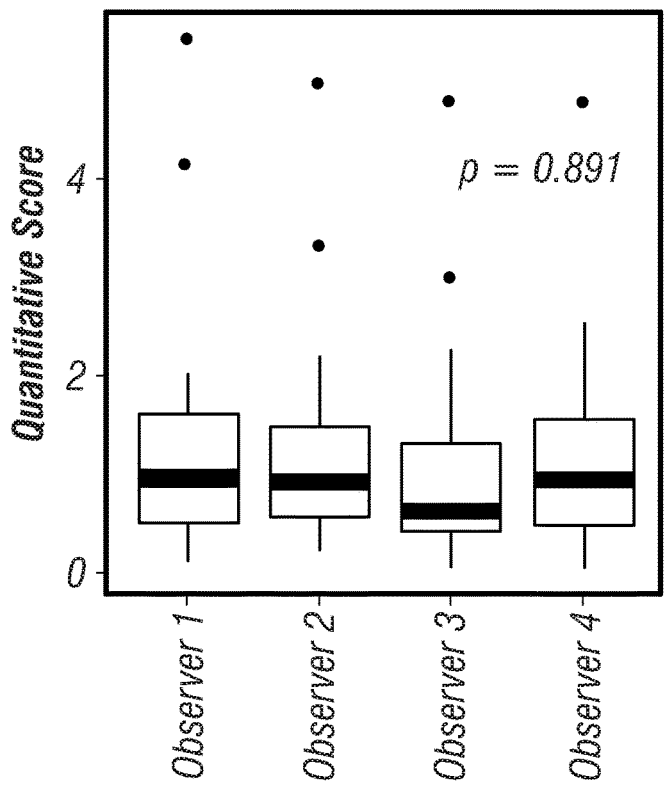

Since both the AP and QS values appeared effective in grade assessment their performance was compared by AUC and logistic linear regression. The AUC analyses identified 27% and 1.7 cut-off points for the AP and QS values respectively as the most optimal for the assessment of low- and high-grade tumors (FIGS. 11A and B). Both parameters were equally effective and the overall accuracy of grade assessment was 83.7%. Both the AP and the QS values predicted high-grade of the tumors with 95% specificity. Correlation analysis showed that both parameters were closely related to each other and performed in a similar fashion thus combining them did not improve the accuracy of the classifier (FIG. 5C).

Finally, the interobserver variability was observed in which 19 cases from the cancer group were independently analyzed by four observers who received brief training concerning the identification of cells in cytologic preparations of voided urine and quantitative inspection of fluorescent signals. The data disclosed some variability among individual observers which was typically within a 10% range of the mean value and the differences among the individual observers were statistically insignificant (FIG. 12A-F).

The multi-color FISH test introduced here, the Quartet Test, is comprised of four distinct chromosomal probes aimed at the specific amplified chromosomal regions of 6p22, 8q22, 11q13, and 20q11.2. These regions were selected by genome-wide CNV analysis of the MD Anderson and TCGA cohorts. The data from these two cohorts were overlapping but not identical. Because the TCGA cohort is restricted to high grade muscle invasive bladder cancer, it is not ideal to validate the chromosomal amplicons involved in the full spectrum of bladder cancers. In order to address this issue the data from Chekaluk et al. was included in the selection process who analyzed genome-wide CNVs of both invasive and superficial papillary subsets of bladder cancers, which contain three of the four amplified regions identified in the MD Anderson and TCGA cohorts. Most importantly, it included an amplicon on chromosome 11q13. Test results were analyzed using either AP or QS. The AP Quartet Test detected bladder cancer with 93.8% specificity and 78.6% sensitivity. The QS Quartet Test provides additional information concerning tumor grade, and was helpful in identifying patients with high-grade and low-grade bladder cancer. The QS Quartet Test detected bladder cancer with 95.8% specificity and 76.85% sensitivity.

TABLE 1

Summary of Clinical and Pathologic Data of Human Subjects Used to Assess the Performance of the Quartet Test (n = 146)

|  | Number of Samples | Gender F | Gender M | Mean Age ± STDEV |
|---|---|---|---|---|
| Urine Samples |  |  |  |  |
| Control Samples | 48 | 22 | 26 | 60.70 ± 11.12 |
| Healthy individuals | 18 | 9 | 9 | 59.17 ± 10.14 |
| Benign disorders | 30 | 13 | 17 | 61.62 ± 11.74 |
| Hematuria | 2 | 2 | 0 | 44.34 ± 3.51 |
| Elevated PSA | 2 | 0 | 2 | 74.08 ± 8.66 |
| Hyperlipidemia/ Hypercholesterolemia | 7 | 1 | 6 | 66.52 ± 9.35 |
| Kidney stone | 1 | 0 | 1 | 55.31 |
| Renal failure | 1 | 0 | 1 | 67.96 |
| Stricture of Ureter | 1 | 0 | 1 | 46.39 |
| Neurogenic bladder | 3 | 3 | 0 | 50.35 ± 7.95 |
| Others | 13 | 7 | 6 | 65.96 ± 9.24 |
| Tumor Samples | 98 | 23 | 75 | 66.00 ± 12.56 |
| LGPUC* (Ta-T1a) | 56 | 16 | 40 | 64.48 ± 12.57 |
| HGUC ** (T1b-higher) | 42 | 7 | 35 | 68.01 ± 12.41 |
| Total | 146 | 45 | 101 | 64.26 ± 12.32 |

*LGPUC—low grade papillary urothelial carcinoma;
** HGUC—high grade urothelial carcinoma;

Example 2—Materials and Methods

Figure 7:
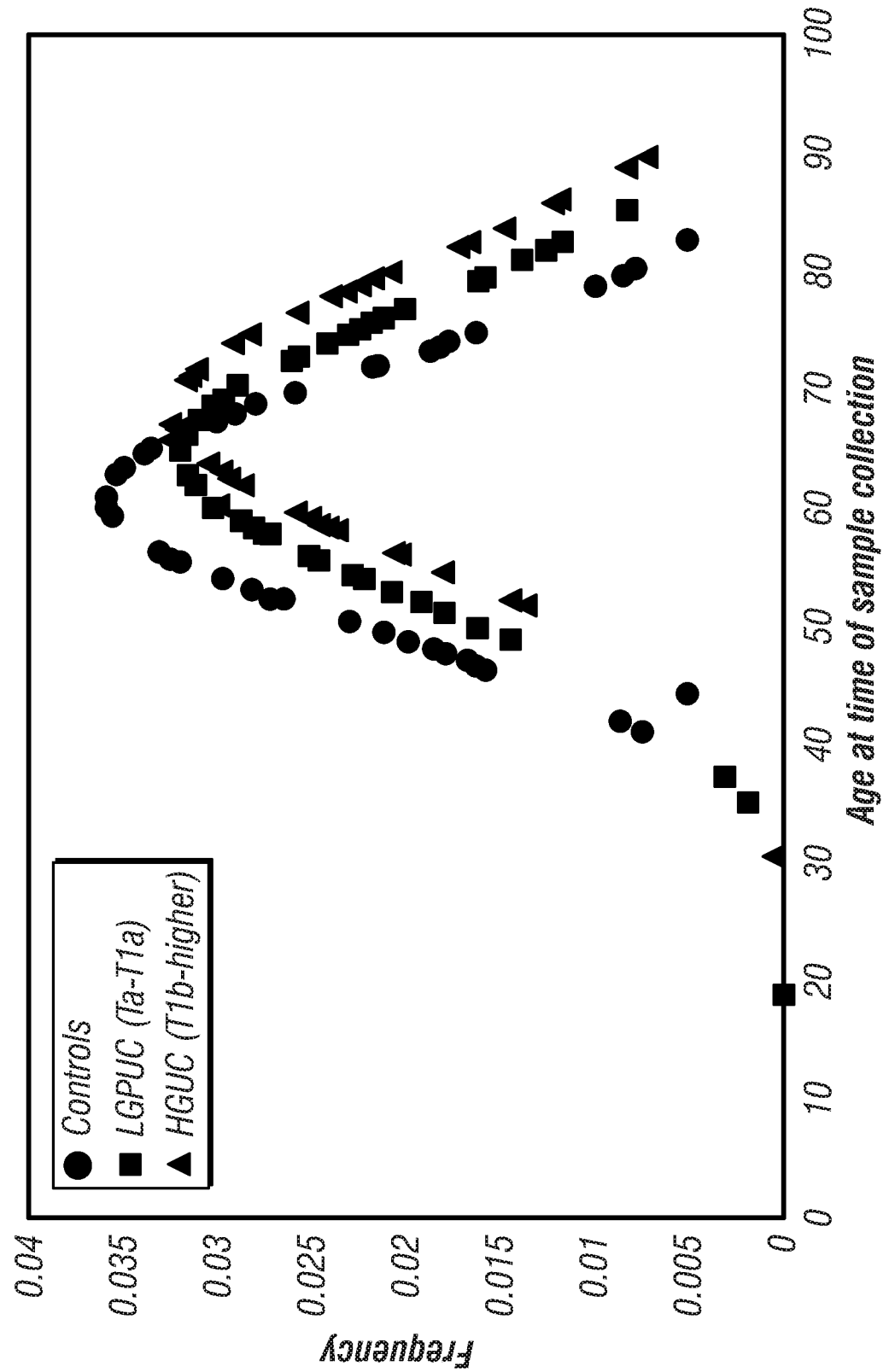
FIG. 7: Age distribution patterns of three distinct cohorts of patients whose voided urine samples were tested by the Quartet Test.

Patients and Tissue Samples. All human tissues used in this study were collected under protocols reviewed and approved by the Institutional Review Board of The University of Texas MD Anderson Cancer Center (MDACC) and collaborating institutions. Informed consent was obtained from all subjects who provided tissue samples and urine for this study. All studies were performed in accordance with the relevant guidance and regulations. Genome-wide copy number variations were initially assayed in paired fresh frozen bladder tumor and normal peripheral blood samples from 40 patients, including 14 with low-grade papillary (LGPUC) disease (Ta-T1a) and 26 with high-grade invasive (HGUC) disease (T1b-higher) tumor samples. The copy number variants identified in the MDACC cohort were then validated in the initially published The Cancer Genome Atlas (TCGA) cohort containing 129 samples from high-grade muscle invasive conventional urothelial carcinoma of the bladder (Cancer Genome Atlas, 2014). The performance of probes and their specificity for respective chromosomal loci as well as standardization of the hybridization procedures were initially tested on normal human peripheral blood lymphocytes, microscopically normal appearing urothelial cells from ureters of nephrectomy specimens as well as on human metaphase chromosomes (Applied Genetics Laboratories, Inc., Melbourne, Fla.) as previously described (Robertson et al., 2017). The initial testing of standardized mixtures of four FISH probes were performed on paired samples of touch prints from 53 bladder tumor samples (19 LGPUC and 34 HGUC) obtained by transurethral resection and voided urine typically collected 2-3 days before cystoscopy. Final validation of the Quartet Test was performed on voided urine samples from 98 cancer patients, including 56 LGPUC (Ta-T1a) and 42 HGUC (T1b-higher), and 48 controls, including 18 healthy controls and 30 patients with various non-neoplastic disorders. For the patients with bladder cancer, the diagnosis was confirmed by cystoscopy and microscopic examination of the tumor samples. The cancer patients were randomly selected from the pathology data files for the availability of voided urine and pathological samples. For the control group in patients with benign urologic disorders, bladder cancer was ruled out by clinical evaluation and standard urologic diagnostic work-up. The healthy controls were clinically asymptomatic volunteer donors of urine samples. The clinical and pathological data for 146 human subjects used to assess the performance of the Quartet Test are summarized in Table 1 and FIG. 7. All bladder tumor samples and voided urine from patients with bladder cancer were collected at MDACC, Houston Tex. Voided urine samples of healthy controls and patients with nonneoplastic disorders were collected at The University of Texas Southwestern Medical Center, Dallas, Tex.

Urothelial carcinomas (UC) were classified according to the histologic tumor grading system of the World Health Organization and were dichotomized as low-grade or high-grade tumors (Eble and Sesterhenn, 2004). The growth pattern of papillary vs non-papillary or solid tumors and the depth of invasion were also recorded. Levels of invasion were defined according to the TNM staging system. T1 tumors were sub-staged as T1a or T1b to divide them into superficial (Ta-T1a) or invasive (T1b and higher) as previously described (Park et al., 2008). The tumors from both MDACC and TCGA datasets included only pure conventional urothelial carcinomas. The bladder cancer variants were not included in this study.

Copy Number Variation Analysis and Design of Quartet Test. Copy number variation (CNV) analysis was performed using two-sample Illumina Human 1M-Duo V1 DNA analysis BeadChips which interrogate more than 1.1 million loci per sample. For CNV analysis DNA was extracted from paired fresh frozen bladder tumor and peripheral blood samples from 40 cancer patients as previously described. Arrays were prepared according to the Infinium II Assay protocol and scanned the same day using an Illumina BeadArray Reader 500G. The microarray data from the MDACC and TCGA cohorts were imported into the SNP genotyping module in the Illumina Genome Studio software to perform CNV analysis. These analyses identified the most frequently amplified chromosomal loci; we combined these with their respective gene content to design the Quartet Test. In selecting the chromosomal loci to interrogate with FISH probes, we used both the frequency and the degree of their amplification in bladder cancer as well as their genomic content in terms of the specific genes and repetitive sequences. In addition, other published data concerning the CNV analysis were included in the selection of the probes (Chekaluk et al., 2013). Using these factors, probes for the following regions (listed with their respective fluorescent tags) were selected and provided by Kreatech/Leica (Buffalo Grove, Ill.): 6p22, E2F3—CDKAL1, 525 KB, green, Platinum Bright™495; 8q22. PABPC1-ZNF706, 480 KB, gold, Platinum Bright™530; 11q13, FGF19-FGF3, dark red, Platinum Bright™590; and 20q11.2, MAPRE1, 610 KB, blue, Platinum Bright™415. The probes were produced from their respective BAC clones using REPEAT-FREE™ FISH technology and were labeled with their respective fluorochromes by the universal linkage system method.

Tumor Samples and Urine Analyzed by FISH. Voided urine specimens (approximately 200 ml) were collected and prepared for FISH analysis as previously described (Park et al., 2008). In brief, the urine was centrifuged for 15 minutes at 200 g and the resulting pelleted material containing exfoliated tumor cells was re-suspended in 2 ml of Dulbecco's modified Eagle medium (DMEM, Invitrogen, Carlsbad, Calif.) containing 10% dimethyl sulfoxide and stored at −70° C. For FISH analysis, frozen sediment samples containing exfoliated cells were defrosted, washed 3 times in PBS and cytospun onto slides. The cytospin preparations were fixed in methanol:acetic acid (3:1), pretreated in 2× saline sodium citrate (SSC) buffer at 37° C. for 30 minutes and then dehydrated in increasing concentrations of ethanol. The slides were heated at 90° C. for 5 minutes to denature the DNA and then incubated overnight at 37° C. with a mixture of the four FISH probes. After hybridization, the slides were washed with 0.5×SSC with 0.1% sodium dodecyl sulfate at 65° C., counterstained with 4',6-diamidino-2-phenylindole (DAPI) (Invitrogen), mounted with an antifade solution (Roche Diagnostics, Mannheim, Germany) and coverslipped. Fluorescent signals were counted and photographed using a Leica Fluorescent Microscope and Image Analysis System (Leica CytoVision DM5500).

Data Analysis. Samples were scored for abnormality in two ways. The first, "abnormal proportion" (AP) score, is simply the proportion of the cells examined which showed any visible abnormality. The second, "quantitative score" (QS), includes not only the proportion of cells with abnormal copy numbers but also the proportions of cells with numbers of altered copies and their degree of amplification calculated as follows:

$$QS = \frac{(n_{cells\,altered} + n_{cells>4\,copies}) * n_{probes\,altered}}{n_{cells}}$$

Receiver operator characteristic (ROC) curves to identify cutoff values for the scores at which the joint performances (sensitivity+specificity) were maximized. The area under the ROC curve (AUC) to assess the performance of the Quartet Test to detection bladder cancer. Interval estimates for the AUC values were computed using 1000 bootstrap simulations. In each simulation, one bootstrap sample was drawn from the group of controls, another bootstrap sample was drawn from the group of cancer cases, and the AUC for these two groups was computed. The 1000 values obtained were sorted, and the 25th and 975th values comprise the interval reported. A Wilcoxon-Mann-Whitney rank sum test was used to compare the case and control groups. Interval estimates for proportions (sensitivity and specificity) used the $2.5_{th}$ and $97.5_{th}$ percentiles of a beta distribution proportional to the likelihood function. In follow-up analyses comparing abnormality scores between cohorts, the statistical significance of differences between mean values was tested by unpaired two sample t-tests or Wilcoxon rank sum tests. Comparisons involving three or more groups or multiple factors were performed using analysis of variance. Linear discrimination was used to determine the performance of the proportion of the abnormal cells and QS in the assessment of tumor grades and leave-one-out cross validation was employed to evaluate the performance of the classifiers. All statistical tests were two-sided. P less than or equal to 0.05 was considered statistically significant. Copy number gains were reported as categorical integer values (roughly log 2 scale) by the Illumina Genome Studio software: 0=diploid, 1=amplification, 2=marked amplification. Data analysis and calculations were performed using R Package Software (version 3.3.2).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Cancer Genome Atlas Research N. *Nature* 507:315-22, 2014.
Chekaluk et al., *PLoS One* 8:e60927, 2013.
Dal Moro et al., *Urologia.* 80:265-75, 2013.
Eble and Sesterhenn, *WHO/OMS IARCPress* 2004.
Grossman et al. *The New England Journal of Medicine* 349, 859-866, 2003.
International Patent Publication No. WO2006/121168
International Patent Publication No. WO2009/114335
International Patent Publication No. CLAIMSWO2015016718
Leitch et al., In Situ Hybridization: a practical guide, Oxford BIOS Scientific Publishers, Microscopy handbooks 27, 1994.
Mazzucchelli et al., *Anal Quant Cytol Histol.* 27:143-51, 2005.
Naylor and van Deursen. *Annu Rev Genet.* 50:45-66, 2016.
Nikonova et al., *Cell Mol Life Sci.* 70:661-87, 2013.
Park, H. S. et al., *Journal of the National Cancer Institute* 100, 1401-1411, 2008.
Phillips and Richardson, *BJU Int.* 98:33-7, 2006.
Robertson et al., *Cell* 2017.
Sansregret and Swanton, *Cold Spring Harb Perspect Med.* 7, 2017.
Shah et al., *Clinical Cancer Research* 17, 2608-2612, 2011.
Spiess and Czerniak, *Archives of Pathology & Laboratory Medicine* 130, 844-852, 2006.
Sternberg et al., *European Urology* 63, 58-66, 2013.
U.S. Pat. No. 5,491,224
U.S. Pat. No. 5,776,688
U.S. Pat. No. 6,207,156
U.S. Pat. No. 8,008,449
U.S. Pat. No. 8,017,114
U.S. Pat. No. 8,119,129
U.S. Pat. No. 8,354,509
U.S. Pat. No. 8,735,553
U.S. Patent Publication No. US20110008369
U.S. Patent Publication No. US2014022021
U.S. Patent Publication No. US20140294898
U.S. Patent Publication No. US2005/0100944
US Patent Publication US2006/0199213

What is claimed is:

1. An in vitro method of quantifying the copy number of four probes comprising:
   (a) obtaining a set of locus-specific probes for 6p22.3 spanning E2F3 to CDKAL1, 8q22 spanning PABPC1 to ZNF706, 11q13.1 spanning FGF19 to FGF3, and 20p11.2 spanning MAPRE1;
   (b) hybridizing the set of locus-specific probes to a plurality of nucleic acids in urothelial cells in a voided urine sample to perform fluorescence in situ hybridization (FISH); and
   (c) analyzing the hybridization pattern of the set of locus-specific probes to the plurality of nucleic acids, thereby quantifying the copy number of the four probes.

2. A method of treating bladder cancer in a subject comprising:
   (a) performing fluorescence in situ hybridization (FISH) on a human sample obtained from the subject using locus-specific probes for 6p22, 8q22, 11q13, and 20p11.2;
   (b) identifying the subject as having bladder cancer by quantifying the copy number of the loci 6p22, 8q22, 11q13, and 20p11.2, wherein an abnormal copy number of three or more copies at each of the loci 6p22, 8q22, 11q13 and 20p11.2 identifies the subject as having bladder cancer; and
   (c) administering an effective amount of one or more anti-cancer therapies to the subject identified to have bladder cancer.

3. The method of claim 2, wherein the sample is a voided urine sample.

4. The method of claim 2, wherein the one or more anti-cancer therapies are chemotherapy, radiotherapy, gene therapy, surgery, hormonal therapy, anti-angiogenic therapy, and/or immunotherapy.

5. The method of claim 2, wherein the anti-cancer therapy is a molecularly targeted therapy.

6. The method of claim 2, wherein each probe is labeled with a distinct fluorophore.

7. The method of claim 6, wherein the distinct fluorophores are green, gold, red, and blue.

8. The method of claim 6, wherein the distinct fluorophores have excitation at 495 nm, 530 nm, 590 nm, and 415 nm.

9. The method of claim 2, wherein an abnormal copy number of all four of the locus-specific probes indicates a high grade tumor.

10. The method of claim 2, wherein at least 15% of cells in the sample comprise the abnormal copy number.

11. The method of claim 2, wherein the sensitivity of detecting bladder cancer is at least 75%.

12. The method of claim 2, wherein the locus-specific probes are 6p22.3, 8q22, 11q13.1, and 20p11.2.

* * * * *